US010639293B2

(12) United States Patent
Zygmunt et al.

(10) Patent No.: US 10,639,293 B2
(45) Date of Patent: May 5, 2020

(54) 9,10-α,α-OH-TAXANE ANALOGS AND METHODS FOR PRODUCTION THEREOF

(71) Applicant: Tapestry Pharmaceuticals, Inc., Atlanta, GA (US)

(72) Inventors: Jan Zygmunt, Longmont, CO (US); James Ferrara, Boulder, CO (US); James D. McChesney, Etta, MS (US)

(73) Assignee: Tapestry Pharmaceuticals, Inc., Atlanta, GA (US)

( * ) Notice: Subject to any disclaimer, the term of this patent is extended or adjusted under 35 U.S.C. 154(b) by 0 days.

(21) Appl. No.: 16/247,425

(22) Filed: Jan. 14, 2019

(65) Prior Publication Data

US 2019/0142784 A1 May 16, 2019

Related U.S. Application Data

(63) Continuation of application No. 15/728,049, filed on Oct. 9, 2017, which is a continuation of application
(Continued)

(51) Int. Cl.
*A61K 31/337* (2006.01)
*C07D 409/12* (2006.01)
(Continued)

(52) U.S. Cl.
CPC .......... *A61K 31/337* (2013.01); *A61K 31/357* (2013.01); *C07D 305/14* (2013.01);
(Continued)

(58) Field of Classification Search
CPC ...................................................... A61K 3/337
(Continued)

(56) References Cited

U.S. PATENT DOCUMENTS 5,352,806 A 10/1994 Gunawardana
5,635,531 A 6/1997 Chen
(Continued)

FOREIGN PATENT DOCUMENTS

EP 856512 A2 8/1998
EP 1148055 A1 10/2001
(Continued)

OTHER PUBLICATIONS

Gunda I. Georg et al. "The Chemistry of the Taxane Diterpene: Stereoselective Reductions of Taxanes." Journal of Organic Chemistry., vol. 63, No. 24, 1998, pp. 8926-8934, XP002393381 US American Chemical Society.
L. L. Klein "Synthesis of 9-Dihydrotaxol: A Novel Bioactive Taxane" Tetrahedron Letters, Elsevier, Amsterdam, NL, vol. 34, No. 13, 1993, pp. 2047-2050, XP000943602 ISSN: 0040-4039.
L. L. Klein et al. "Antitumor Activity of 9(R)-Dihydrotaxane Analogs" Journal of Medicinal Chemistry, American chemical Society. Washington, Us, vol. 38, No. 9, Apr. 28, 1995 (Apr. 28, 1995), pp. 1482-1492, XP002111770 ISSN: 0022-2623.
A. Datta et al. "Synthesis of Novel C-9 and C-10 Modified Bioactive Taxanes" Tetrahedron Letters, Elsevier, Amsterdam, NL, vol. 36, No. 12, Mar. 20, 1995 (Mar. 20, 1995), pp. 1985-1988, XP000491694 ISSN: 0040-4039.
(Continued)

*Primary Examiner* — Taofiq A Solola
(74) *Attorney, Agent, or Firm* — Morgan, Lewis & Bockius LLP

(57) ABSTRACT

The present invention relates to a method for the treatment of cancer in a cancer patient. In particular, the invention provides a method for the treatment comprising administering a taxane compound to a cancer patient, wherein the taxane compound is made by a process comprising treating a first compound represented by either Formula G' or Formula M':

with a second compound of generalized formula $R_8R_9C(OCH_3)_2$ and an acid selected from the group consisting of camphor sulfonic acid (CSA), p-toluene sulfonic acid (PTSA), hydrochloric acid (HCl) and acetic acid (AcOH), wherein $R_1$ and $R_2$ are each selected from H, an alkyl group, an olefinic group, an aromatic group, an O-alkyl group, an O-olefinic group, or an O-aromatic group; $R_7$ is an alkyl group, an olefinic group, or an aromatic group; $P_1$ is a hydroxyl protecting group; $P_5$ is H or an acid labile protecting group at the 7-O position; $R_8$ is H, alkyl group, olefinic or aromatic group; and $R_9$ is: H, alkyl group, olefinic or aromatic or is as defined in the specification.

10 Claims, 23 Drawing Sheets

Related U.S. Application Data

No. 15/220,975, filed on Jul. 27, 2016, now Pat. No. 9,820,962, which is a continuation of application No. 14/604,147, filed on Jan. 23, 2015, now Pat. No. 9,402,824, which is a continuation of application No. 12/954,253, filed on Nov. 24, 2010, now Pat. No. 8,962,870, which is a continuation of application No. 12/792,427, filed on Jun. 2, 2010, now Pat. No. 7,879,904, which is a continuation of application No. 10/951,555, filed on Sep. 27, 2004, now Pat. No. 7,745,650.

(60) Provisional application No. 60/506,680, filed on Sep. 25, 2003.

(51) Int. Cl.
*C07D 305/14* (2006.01)
*C07D 493/08* (2006.01)
*A61K 31/357* (2006.01)

(52) U.S. Cl.
CPC ........ *C07D 409/12* (2013.01); *C07D 493/08* (2013.01); *Y02P 20/55* (2015.11)

(58) Field of Classification Search
USPC ........................................................ 514/452
See application file for complete search history.

(56) References Cited

U.S. PATENT DOCUMENTS

| | | | |
|---|---|---|---|
| 5,739,359 | A | 4/1998 | Kingston et al. |
| 6,048,990 | A | 4/2000 | Liang et al. |
| 6,710,191 | B2 | 3/2004 | Holton et al. |
| 6,794,523 | B2 | 9/2004 | Holton et al. |
| 6,898,834 | B1 | 5/2005 | Warren |
| 7,153,946 | B2 | 12/2006 | McChesney |
| 7,745,650 | B2 | 6/2010 | Zygmunt |
| 7,879,904 | B2 | 2/2011 | Zygmunt |
| 8,962,870 | B2 | 2/2015 | Zygmunt |
| 2002/0198141 | A1 | 12/2002 | McChesney |
| 2005/0148657 | A1 | 7/2005 | Zygmunt |
| 2005/0209174 | A1 | 9/2005 | McChesney |
| 2007/0225510 | A1 | 9/2007 | Henri |
| 2008/0207743 | A1 | 8/2008 | Lamb |
| 2008/0207744 | A1 | 8/2008 | McChesney |
| 2008/0269319 | A1 | 10/2008 | McChesney |
| 2009/0156828 | A1 | 6/2009 | Henri |
| 2009/0246211 | A1 | 10/2009 | Henri |
| 2009/0306400 | A1 | 12/2009 | Henri |
| 2010/0069643 | A1 | 3/2010 | McChesney |
| 2010/0324128 | A1 | 12/2010 | Zygmunt et al. |

FOREIGN PATENT DOCUMENTS

| | | | |
|---|---|---|---|
| EP | 1228759 | A2 | 8/2002 |
| EP | 1285920 | A1 | 2/2003 |
| EP | 1664033 | A2 | 6/2006 |
| EP | 1785416 | A2 | 5/2007 |
| EP | 1810968 | A2 | 7/2007 |
| EP | 1894921 | A2 | 3/2008 |
| EP | 1973892 | A1 | 10/2008 |
| EP | 2007739 | A2 | 12/2008 |
| FR | 2707293 | A1 | 1/1995 |
| FR | 2715846 | A1 | 8/1995 |
| JP | H07505887 | A | 6/1995 |
| WO | WO1992009589 | A1 | 6/1992 |
| WO | WO1993021173 | A1 | 10/1993 |
| WO | WO1994008984 | A1 | 4/1994 |
| WO | WO1994010996 | A1 | 5/1994 |
| WO | WO1994020485 | A1 | 9/1994 |
| WO | WO1995001969 | A1 | 1/1995 |
| WO | WO1996029321 | A1 | 9/1996 |
| WO | WO2001056564 | A1 | 8/2001 |
| WO | WO2001057027 | A1 | 8/2001 |
| WO | WO2005030150 | A1 | 4/2005 |
| WO | WO2006124737 | A1 | 11/2006 |
| WO | WO2007073383 | A1 | 6/2007 |
| WO | WO2003053350 | A2 | 7/2007 |
| WO | WO2007075870 | A2 | 7/2007 |
| WO | WO2007126893 | A1 | 11/2007 |
| WO | WO2007126893 | A2 | 11/2007 |
| WO | WO2008106621 | A1 | 9/2008 |
| WO | WO2008109360 | A1 | 9/2008 |
| WO | WO2008121476 | A1 | 10/2008 |

OTHER PUBLICATIONS

J. Demattei et al. "An Efficient Synthesis of the Taxane-Derived Anticancer Agent ABT-271" Journal of Organic Chemistry, vol. 66, No. 10, 2001, pp. 3330-3337, XP002393380 US American Chemical Society, Easton.

S.M. Ali et al. "Novel Cytotoxic 3'-(Tert-Butyl)3'-Dephenyl Analogs of Paclitaxel and Docetaxel" J. Med. Chem., vol. 38, 1995, pp. 3821-3828, XP003001668.

M.E. Bunnage et al.. "Asymmetric Synthesis of Anti-(2S,3S)- and Syn-(2R,3S)-Diyminobutanoic Acid" Org. Biomol. Chem., vol. 1, No. 21, 2003, pp. 3708-3715, XP003001669.

E. Baldelli et al. "New Taxane Derivatives: Synthesis of Baccatin [14,1-D]Furan-2-One Nucleus and Its Condensation With the Norstatine Side Clain" J. Org. Chem., vol. 69, No. 20, 2004, pp. 6610-6616, XP003001670.

G. Appendino et al. "The Reductive Fragmentation of 7-Hydroxy-9,10-Dioxotaxoids" European Journal of Organic Chemistry, Wiley-VCH Verlag, Weinheim, DE, No. 22, 2003, pp. 4422-4431, XP002395174 ISSN: 1434-193X.

G. Appendino et al. "The Chemistry and Occurrence of Taxane Derivatives. XIII. The Oxidation of 10-Deacetylbaccatin III" Gazzetta Chimica Italiana, Societa Chimica Italiana, Rome, IT, vol. 124, No. 6, Jun. 1, 1994 (Jun. 1, 1994), pp. 253-257, XP000571759 ISSN: 0016-5603.

E. Didier et al. "2-Monosubstituted-1,3-Oxazolidines as Improved Protective Groups of N-Boc-Phenylisoserine in Docetaxel Preparation" Tetrahedron Letters, Elsevier, Amsterdam, NL, vol. 35, No. 15, 1994, pp. 2349-2352, XP001021493 ISSN: 0040-4039.

G. Pratesi et al. "IDN5109 a New Taxane Active After Oral Administration" Proceedings of the American Association for Cancer Research Annual Meeting, vol. 40, Mar. 1999 (Mar. 1999), p. 287, XP001536946 & 90th Annual Meeting of the American Association for Cancer Research; Philadelphia, Pennsylvania, USA; Apr. 10-14, 1999 ISSN: 0197-016X.

A. M. Omuro et al. "Vinorelbine Combined With a Protracted Course of Temozolomide for Recurrent Brain Metastases: A Phase I Trial" Journal of Neuro-Oncology Jul. 2006 Us, vol. 78, No. 3, Jul. 2006 (Jul. 2006), pp. 277-280, XP002486093 ISSN: 0167-594x 1573-7373.

M. Johansen et al. "Phase I Evaluation of Oral and Intravenous Vinorelbine in Pediatric Cancer Patients: A Report From the Children's Oncology Group" Clinical Cancer Research Jan. 15, 2006 US, vol. 12, No. 2, Jan. 15, 2006 (Jan. 15, 2006), pp. 516-522, XP002486094 ISSN: 1078-0432.

S. Hofer et al. "Chemotherapy for Malignant Brain Tumors of Astrocytic and Oligodendroglial Lineage" Journal of Cancer Research and Clinical Oncology 2001 De, vol. 127, No. 2, 2001, pp. 91-95, XP002486095 ISSN: 0171-5216.

J. Kobayashi et al. "Effects of Taxoids From Taxus Cuspidata on Microtubule Depolymerization and Vincristine Accumulation in MDR Cells" Bioorganic and Medicinal Chemistry Letters 1997, vol. 7, No. 4, Feb. 18, 1997 (Feb. 18, 1997), pp. 393-398, XP002486096 ISSN: 0960-894X.

G. Samaranayake et al. "Modified Taxols. 5. Reaction of Taxol With Electrophilic Reagents and Preparation of a Rearranged Taxol Derivative With Tubulin Assembly Activity" Journal of Organic Chemistry, American Chemical Society, Easton, vol. 56, Jan. 1, 1991 (Jan. 1, 1991), pp. 5114-5119, XP009005003 ISSN: 0022-3263.

(56) References Cited

OTHER PUBLICATIONS

G. L. Lange et al. "An Approach to the A/B Substructure of 11(15→1)-Abeotaxanes. A Formal Synthesis of Compressanolide" Tetrahedron Letters, Elsevier, Amsterdam, vol. 39, No. 22, May 28, 1998 (May 28, 1998), pp. 3639-3642, XP004118700 ISSN: 0040-4039.
G. I. Georg "Synthesis of Biologically Active Taxol Analogues With Modified Phenylisoserine Side Chains" J. Med. Chem. 1992, 35(22):4230-7.
Iwao Ojima et al. "Syntheses of New Fluorine-Containing Taxoids by Means of beta-Lactam Synthon Method" Tetrahedron Letters 1996, 52(1), 209-234.
Christophe Lucatelli et al. "Synthesis of C-3' Methyl Taxotere (Docetaxel)" The Journal of organic chemistry 2002, 67(26), 9468-9470.
Ojima Iwao et al. "Structure-Activity Relationship Study of Taxoids for Their Ability to Activate Murine Macrophages as Well as Inhibit the Growth of Macrophage-Like Cells" Bioorganic & Medicinal Chemistry 2003,11(13), 2867-2888.
Jean Noel Denis et al. "Direct, Highly Efficient Synthesis from (S)-(+)-Phenylglycine of the Taxol and Taxotere Side Chains" J. Org. Chem. 1991, 56 (24), pp. 6939-6942.
Jean Noel Denis et al. "An improved Synthesis of the Taxol Side Chain and of RP 56976" J. Org. Chem. 1990, 55 (6), 1957-1959.
Jean Noel Denis et al. "An efficient, Enantioselective Synthesis of the Taxol Side Chain" J. Org. Chem. 1986, 51 (1), 46-50.
Li Deng, and Eric N. Jacobsen "A practical, Highly Enantioselective Synthesis of the Taxol Side Chain via Asymmetric Catalysis" J. Org. Chem. 1992, 57 (15), 4320-4323.
Franklin A. Davis et al. "Asymmetric Synthesis of Sulfinimines: Applications to the Synthesis of Nonracemic Beta-Amino Acids and Alpha-Hydroxyl Beta-Amino Acids" J. Org. Chem. 1992, 57 (24), 6387-6389.
Iwao Ojima et al. "Efficient and practical asymmetric synthesis of the taxol C-13 side chain, N-benzoyl-(2R,3S)-3-phenylisoserine, and its analogs via chiral 3-hydroxy-4-aryl-beta-lactams through chiral ester enolate-imine cyclocondensation" J. Org. Chem. 1991, 56 (5), 1681-1683.
Japanese Patent Application No. 2006-528316, non-final Office action dated Oct. 14, 2010.
Kingston et al. "Synthesis and Biological Evaluation of 1-Deoxypaclitaxel Analogues" J. Org. Chem. 1999, 64, 1814-1822.

U.S. Appl. No. 10/951,555, non-final Office action dated Aug. 27, 2009; 6 pages.
U.S. Appl. No. 10/951,555, non-final Office action dated Mar. 27, 2009; 6 pages.
U.S. Appl. No. 10/951,555, final Office action dated May 22, 2008; 5 pages.
U.S. Appl. No. 10/951,555, non-final Office action dated Mar. 14, 2007; 9 pages.
U.S. Appl. No. 11/680,563, non-final Office action dated Dec. 24, 2008; 9 pages.
U.S. Appl. No. 11/691,024, final Office action dated Apr. 14, 2010; 7 pages.
U.S. Appl. No. 11/691,024, non-final Office action dated Sep. 29, 2009; 5 pages.
U.S. Appl. No. 11/743,849, non-final Office action dated Dec. 31, 2008; 9 pages.
U.S. Appl. No. 11/834,489, final Office action dated Dec. 26, 2007; 19 pages.
U.S. Appl. No. 11/834,489, non-final Office action dated Sep. 14, 2007; 16 pages.
U.S. Appl. No. 12/215,563, non-final Office action dated May 1, 2009; 12 pages.
U.S. Appl. No. 14/604,147, non-final Office action dated Nov. 5, 2015; 9 pages.
Canadian Patent Application No. 2539975, Office Action dated May 10, 2011, 3 pages.
Canadian Patent Application No. 2539975, Office Action dated Sep. 28, 2011, 3 pages.
Japanese Patent Application No. 2006-528316, Notice of Reasons for Rejection dated May 27, 2011, 5 pages.
Japanese Patent Application No. 2010-200399, Notice of Reasons for Rejection dated May 8, 2013, 4 pages.
Japanese Patent Application No. 2011-086840, Official Action dated May 8, 2013, 3 pages.
Japanese Patent Application No. 2014-141964, Notice of Reasons for Rejection dated Jan. 14, 2016, 10 pages.
Japanese Patent Application No. 2014-141964, Notice of Reasons for Rejection dated Jul. 17, 2015, 4 pages.
Japanese Patent Application No. 2014-141964, Notice of Final Rejection dated Sep. 2, 2016, 8 pages.
International Patent Application No. PCT/US04/31816; International Search Report and Written Opinion; dated May 17, 2005; 5 pages.
International Patent Application No. PCT/US04/31816; International Preliminary Report on Patentability; dated Apr. 24, 2006; 3 pages.

$R_7COO=$ (Mono, Bis)

(Bis)

(Bis, Tris)

(Mono, Bis)

(Mono, Bis)

(Mono, Bis)

(Mono, Bis)

(Bis)

(Mono)

(Mono)

(Mono, Bis)

(Bis)

Scheme 5
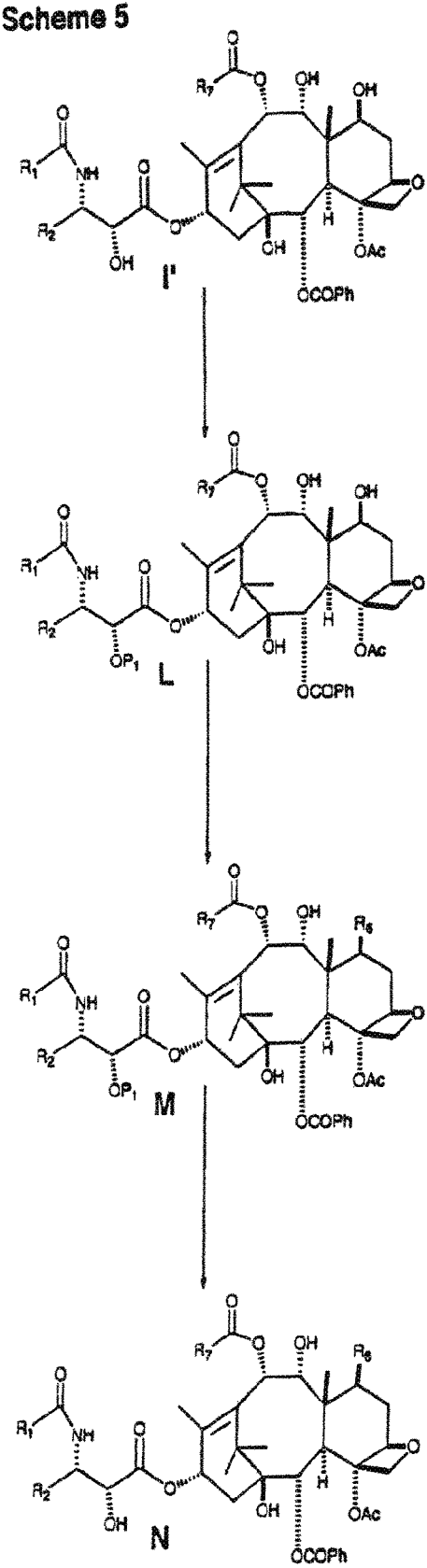
Scheme 6
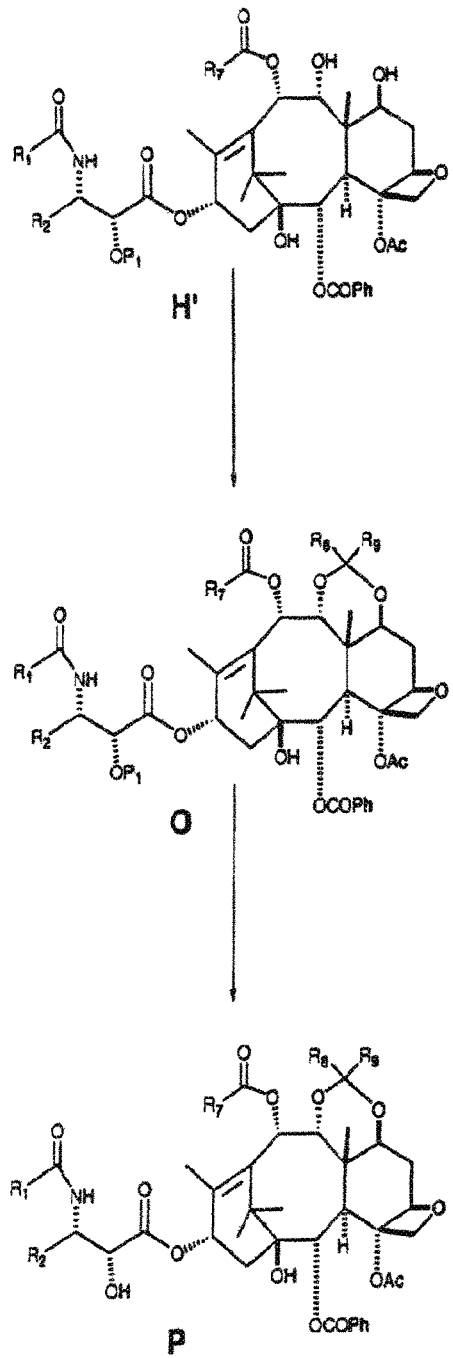
FIG. 7
FIG. 8

Scheme 8

Scheme 9

9,10-α,α-OH-TAXANE ANALOGS AND METHODS FOR PRODUCTION THEREOF

CROSS-REFERENCE TO RELATED APPLICATIONS

This application is a continuation of U.S. patent application Ser. No. 15/728,049 filed Oct. 9, 2017, which is a continuation of U.S. patent application Ser. No. 15/220,975 filed Jul. 27, 2016, which is a continuation of U.S. patent application Ser. No. 14/604,147 filed Jan. 23, 2015, now granted as U.S. Pat. No. 9,402,824, which is a continuation of Ser. No. 12/954,253, filed Nov. 24, 2010, now granted as U.S. Pat. No. 8,962,870, which is in turn a continuation of Ser. No. 12/792,427, filed Jun. 2, 2010, now granted as U.S. Pat. No. 7,879,904, which in turn is a continuation of U.S. patent application Ser. No. 10/951,555, filed Sep. 27, 2004, now granted as U.S. Pat. No. 7,745,650, which in turn claims priority to, and the benefit of, U.S. Provisional Patent Application No. 60/506,680, filed Sep. 25, 2003, all of which are incorporated herein by reference in their entireties.

FIELD OF THE INVENTION

The present invention generally relates to chemical compounds for use in treating cancer patients. More particularly, the present invention is directed to new and useful taxane analogs and methods for producing them. Specifically, the present invention relates to 9,10-α,α-OH taxane analogs, production methods and intermediates useful in the formation thereof.

BACKGROUND OF THE INVENTION

Various taxane compounds are known to exhibit anti-tumor activity. As a result of this activity, taxanes have received increasing attention in the scientific and medical community, and are considered to be an exceptionally promising family of cancer chemotherapeutic agents. For example, various taxanes such as paclitaxel and docetaxel have exhibited promising activity against several different varieties of tumors, and further investigations indicate that such taxanes promise a broad range of potent anti-leukemic and tumor-inhibiting activity.

One approach in developing new anti-cancer drugs is the identification of superior analogs and derivatives of biologically active compounds. Modifications of various portions of a complex molecule may lead to new and better drugs having improved properties such as increased biological activity, effectiveness against cancer cells that have developed multi-drug resistance (MDR), fewer or less serious side effects, improved solubility characteristics, better therapeutic profile and the like.

In view of the promising anti-tumor activity of the taxane family, it is desirable to investigate new and improved taxane analogs and derivatives for use in cancer treatment. One particularly important area is the development of drugs having improved MDR reversal properties. Accordingly, there is a need to provide new taxane compounds having improved biological activity for use in treating cancer. There is also a need to provide methods for forming such compounds. Finally, there is a need for methods of treating patients with such compounds for use in cancer treatment regimens. The present invention is directed to meeting these needs.

SUMMARY OF THE INVENTION

According to the present invention then, new and useful chemical compounds for use in cancer treatment are provided having the formulas:

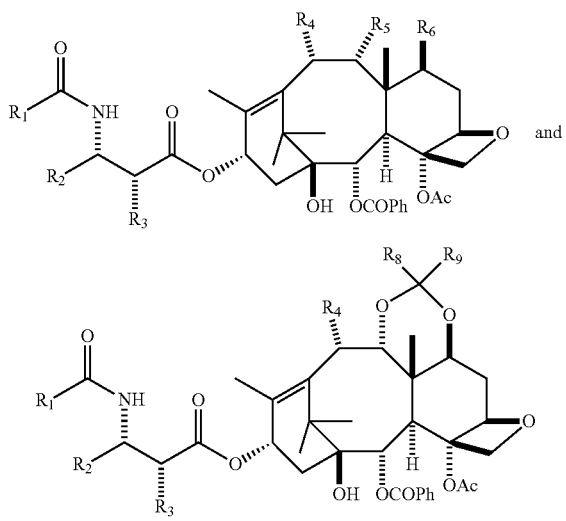

When reference is made to compounds throughout this disclosure, possible $R_x$ groups and $P_x$ groups contemplated hereby are set forth in the following Table 1:

TABLE 1

$R_X$ GROUPS AND $P_X$ GROUPS CONTEMPLATED

| | |
|---|---|
| $R_1$ | H, an alkyl such as an isobutyl group or a tert-butoxyl group, olefinic such as a tiglyl group, aromatic such as a phenyl group, O-alkyl, O-olefinic, or O-aromatic |
| $R_2$ | H, alkyl such as an isobutyl group, olefinic, aromatic group such as Ph, O-alkyl, O-olefinic, or O-aromatic |
| $R_3$ | hydroxyl or $OP_1$ |
| $R_4$ | hydroxyl or $R_7COO$ |
| $R_5$ | hydroxyl or $R_7COO$ |
| $R_6$ | hydroxyl, $OP_2$, $R_7COO$ or an ether functionality such as an O-methylthiomethyl or other hetero substituted ethers |
| $R_7$ | alkyl such as a methyl group, olefinic or aromatic |

$R_7COO$

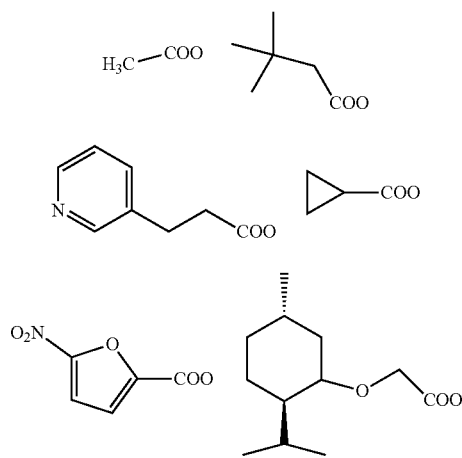

TABLE 1-continued

R_X GROUPS AND P_X GROUPS CONTEMPLATED

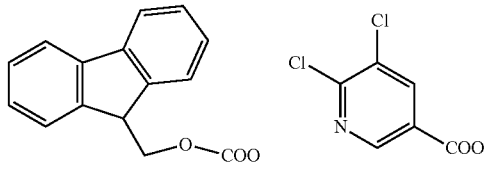
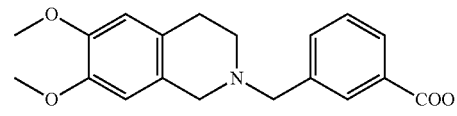
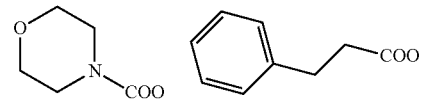
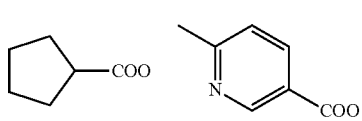
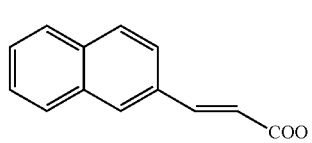
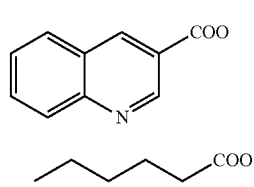

| $R_8$ | H, alkyl group such as a methyl or ethyl group, olefinic or aromatic group |
| --- | --- |
| $R_9$ | H, alkyl group such as a methyl or ethyl group, olefinic or aromatic or may specifically be: |

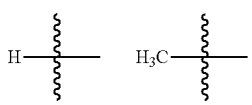
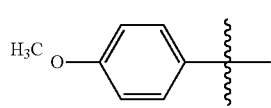
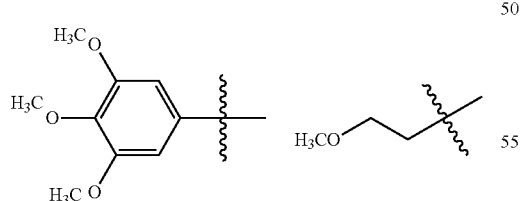
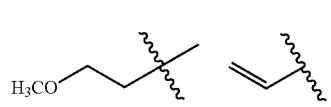
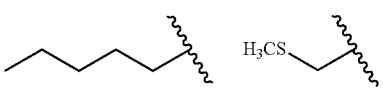

TABLE 1-continued

R_X GROUPS AND P_X GROUPS CONTEMPLATED

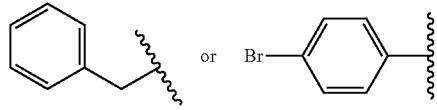 [SMILES: *Cc1ccccc1 ; *c1ccc(Br)cc1]

| $R_{10}$ | alkyl group such as a methyl or ethyl group |
| --- | --- |
| $R_{11}$ | H, alkyl group such as a methyl or ethyl group, olefinic or aromatic group |
| $R_{12}$ | H, alkyl group such as a methyl or ethyl group, olefinic or aromatic or may specifically be: |

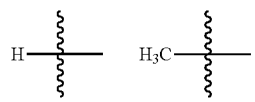
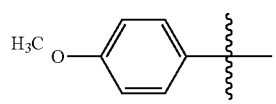
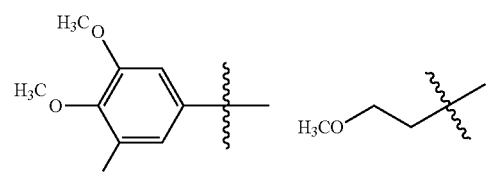
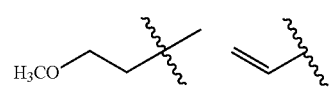
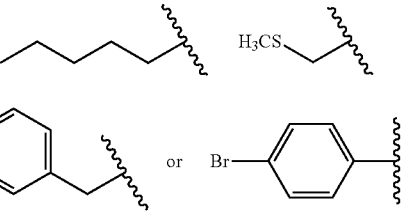

| $R_{13}$ | H, alkyl group such as a methyl or ethyl group, olefinic or aromatic group |
| --- | --- |
| $R_{14}$ | H, alkyl group such as a methyl or ethyl group, olefinic or aromatic or may specifically be: |

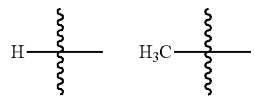
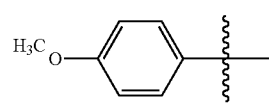
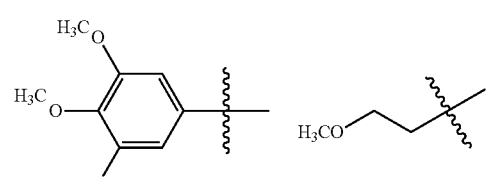
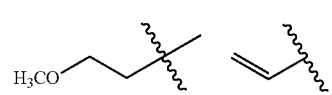

TABLE 1-continued

R$_X$ GROUPS AND P$_X$ GROUPS CONTEMPLATED

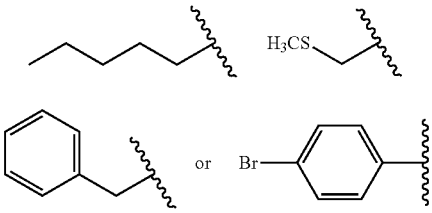

| P$_1$ | hydroxyl protecting group such as a silyl protecting group, for example, TBDMS or TES |
| P$_2$ | hydroxyl protecting group such as a silyl protecting group, for example, TES |
| P$_3$ | NH protecting group such as carbobenzyloxy (CBZ) |

Specifically, R$_1$ may be Ph or tert-butoxyl or tiglyl, R$_2$ may be Ph or isobutyl, R$_6$ may be O-methylthiomethyl or other hetero substituted ethers, P$_1$ may be a silyl protecting group such as TBDMS or TES, and P$_2$ may be a silyl protecting group such as TES. Compounds according to the present invention may be monoacylated at C-10, such as when R$_5$ and R$_6$ are hydroxyl and R$_4$ is R$_7$COO, where R$_7$COO has a formula selected from the following structures:

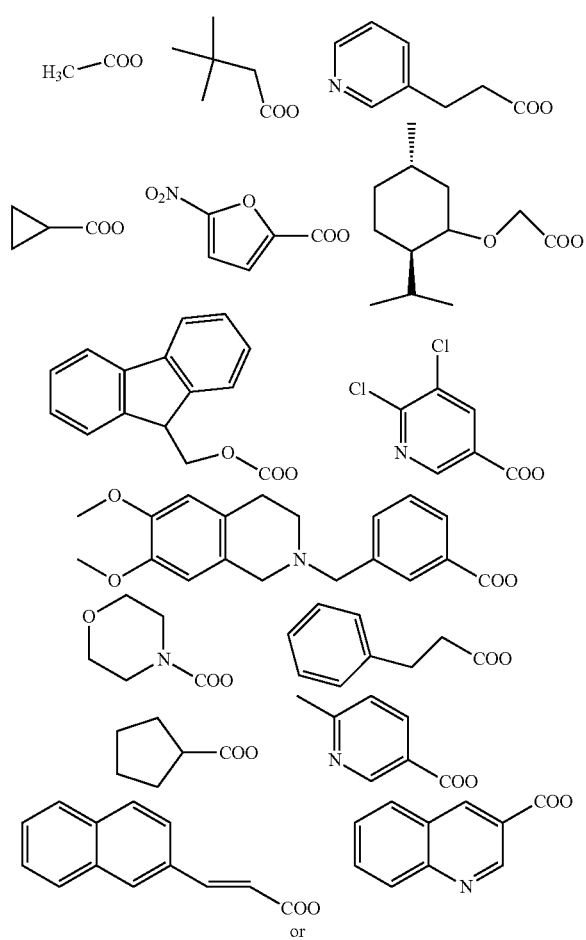

Compounds according to the present invention may alternately be mono-, bis-, or tris-acylated at the 7, 9 and/or 10 positions. For example, R$_6$ may be R$_7$COO when R$_4$ and R$_5$ are hydroxyl; R$_4$ and R$_6$ may both be R$_7$COO when R$_5$ is hydroxyl; or each of R$_4$, R$_5$ and R$_6$ may be R$_7$COO; where R$_7$COO is:

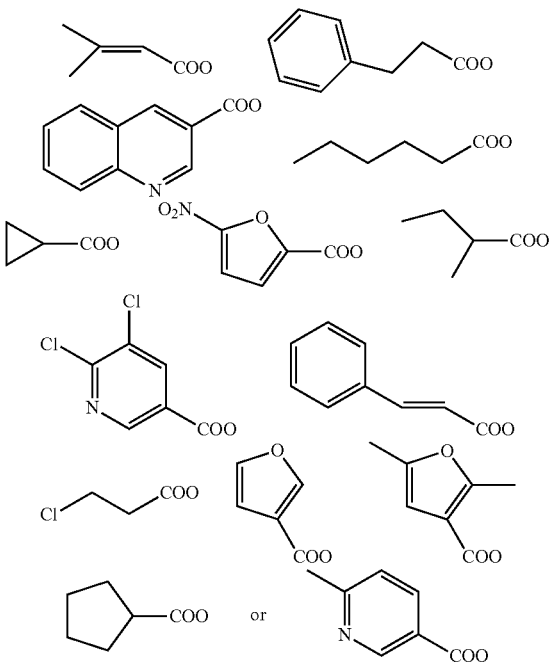

Additionally, chemical compounds according to the present invention may have the formula:

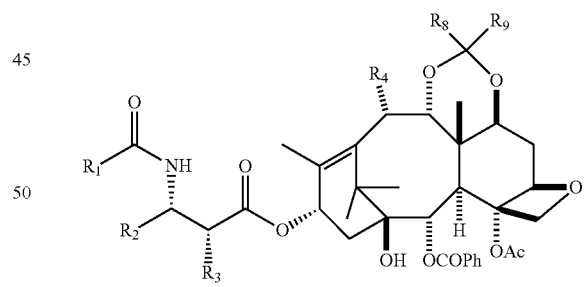

wherein R$_1$ through R$_4$ are as defined in Table 1 above and R$_8$ and R$_9$ are each H, alkyl, olefinic or aromatic. Compounds according to the present invention may be monoacylated at C10, such as when R$_4$ is R$_7$COO, where R$_7$COO is:

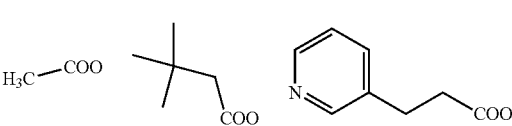

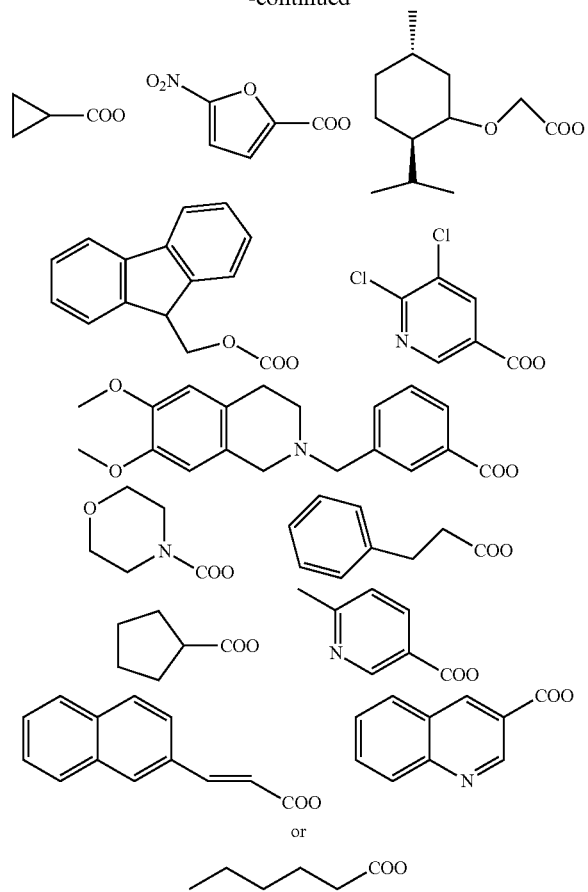

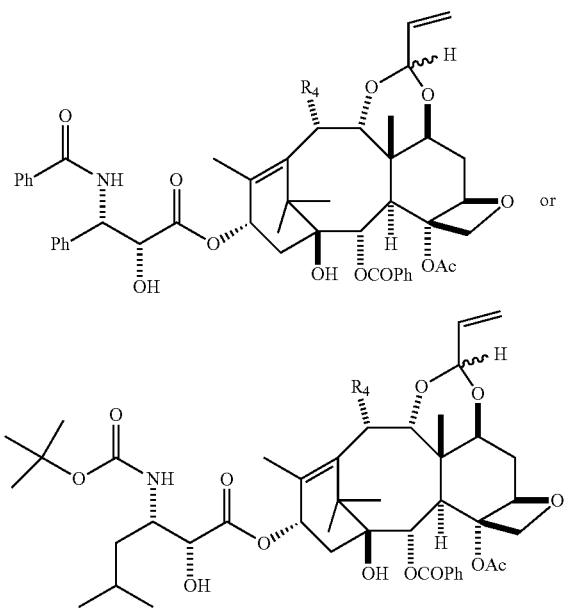

are provided wherein $R_4$ is hydroxyl or $CH_3COO$.

Another example of the 7,9-acetal linked compounds contemplated have the formulas:

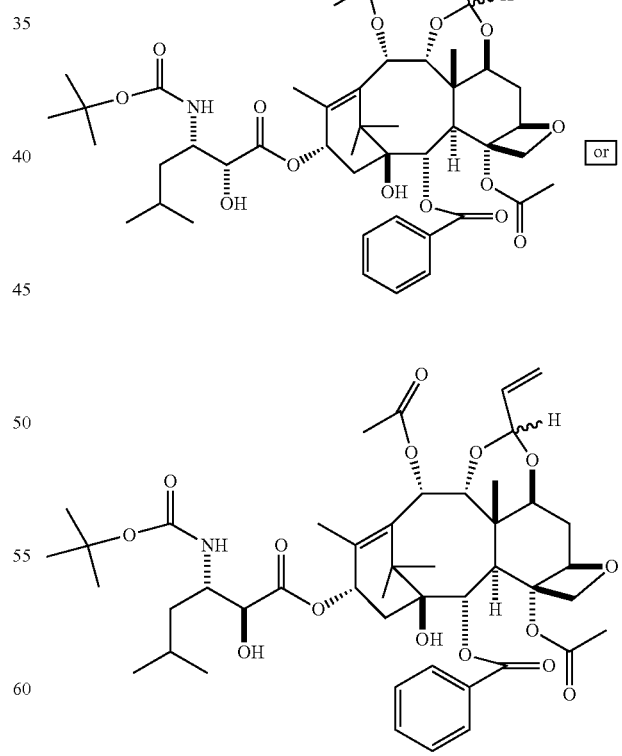

$R_8$ may specifically be H or methyl, and $R_9$ may specifically be:

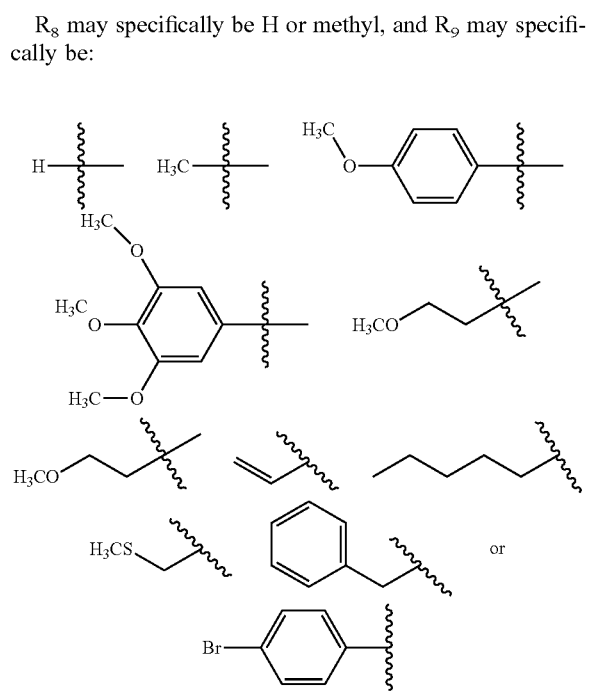

Compounds according to the present invention may have an acroline acetal group connecting the 7,9-positions. For example, chemical compounds of formula:

The present invention also provides intermediates for use in forming compounds useful for cancer treatment, comprising:

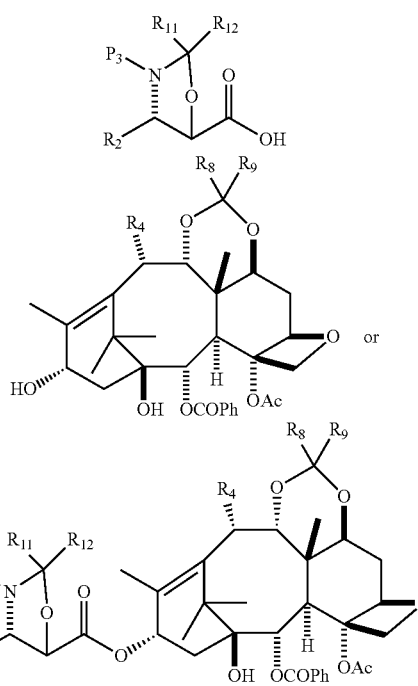

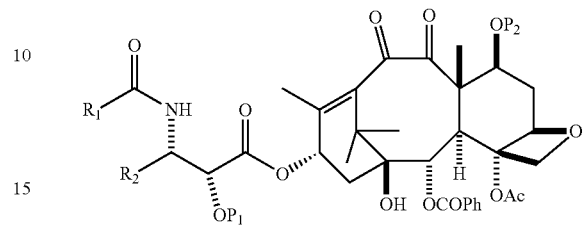

wherein $R_2$, $R_4$, $R_8$ and $R_9$ are as defined in Table 1 above, $P_3$ is a NH protecting group such as carbobenzyloxy (CBZ), and $R_{11}$ and $R_{12}$ are as defined in Table 1 above for $R_8$ and $R_9$, respectively.

The present invention also provides methods for use in producing taxane analogs and derivates thereof for use in cancer treatment. One method according to the present invention comprises providing a starting compound of formula

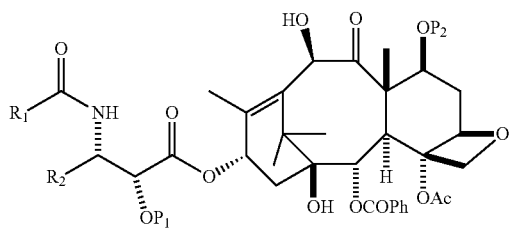

and converting the starting compound into a first taxane analog of the formula

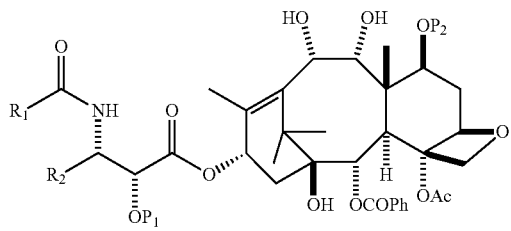

wherein:
  $R_1$ and $R_2$ are each selected from H, an alkyl group, an olefinic group, an aromatic group, an O-alkyl group, an O-olefinic group, or an O-aromatic group;

$R_7$ is an alkyl group, an olefinic group, or an aromatic group; and
  $P_1$ and $P_2$ are each hydroxyl protecting groups;

The starting compound may be oxidized to form a first intermediate compound of the formula The method may further include the step of acylating the first taxane analog at the C-10 position to form a second taxane analog of formula

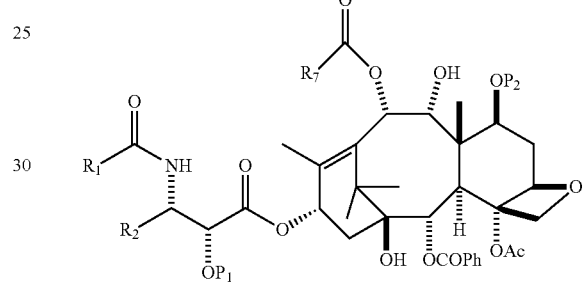

that may thereafter be deprotected, thereby to form a third taxane analog of formula:

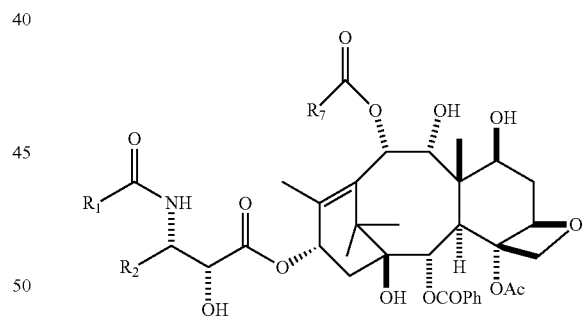

where $R_1$, $R_2$, $R_7$, $P_1$ and $P_2$ are as defined in Table 1 above. The acylation step may be accomplished using a carboxylic acid $R_7COOH$, carboxylic acid halide $R_7COX$, such as an acid chloride, or a carboxyl anhydride $R_7COOCOR_7$. When $P_1$ and $P_2$ are silyl protecting groups such as TES or TBDMS, the step of deprotecting the second taxane analog may be accomplished in a single step using tetrabutylammoniumfluoride (TBAF). Alternatively, the step of deprotecting the second taxane analog may include a first step of deprotecting the second compound at the C-7 position thereby to form a fourth taxane analog of formula:

and then deprotecting the 2'O position of the fourth taxane analog to form a fifth taxane analog of formula:

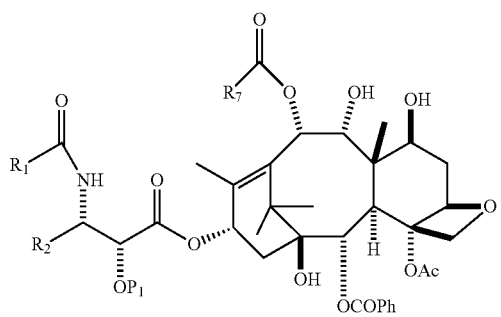

The first step may be accomplished using HF-ACN, and the second step may be accomplished using HF-pyridine.

Alternatively, instead of acylating the first taxane analog, it may be deprotected at the 7-O position to form a sixth taxane analog of formula

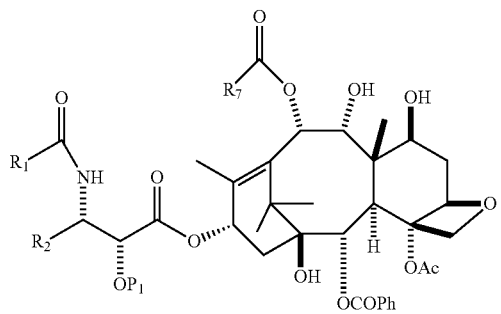

Thereafter the sixth taxane analog may be acylated at the C-7 position, the C-9 position, or the C-10 position to form a seventh taxane analog of formula

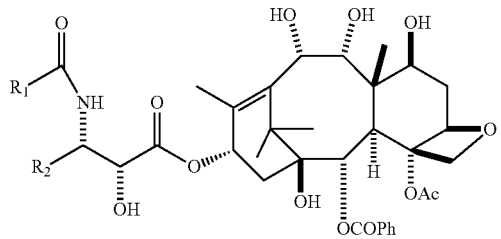

The seventh taxane analog may be deprotected at the 2'0 position to form an eight taxane analog of formula

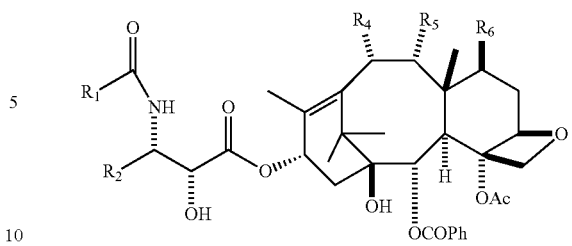

The acylation step of the sixth taxane analog may be accomplished using a carboxylic acid $R_7COOH$, carboxylic acid halide $R_7COX$, such as an acid chloride, or a carboxyl anhydride $R_7COOCOR_7$. Deprotection of the seventh taxane analog at the C-2' position may be accomplished using tetrabutylammoniumfluoride (TBAF).

Another method according to the present invention comprises providing a starting compound of formula

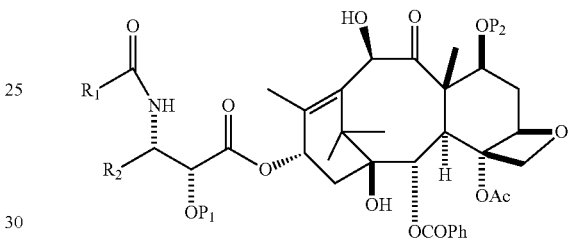

wherein
- $R_1$ and $R_2$ are each selected from H, an alkyl group, an olefinic group, an aromatic group, an O-alkyl group, an O-olefinic group, or an O-aromatic group;
- $R_7$ is an alkyl group, an olefinic group, or an aromatic group; and
- $P_1$ and $P_2$ are each hydroxyl protecting groups;

The starting compound may be converted into a first taxane analog of formula

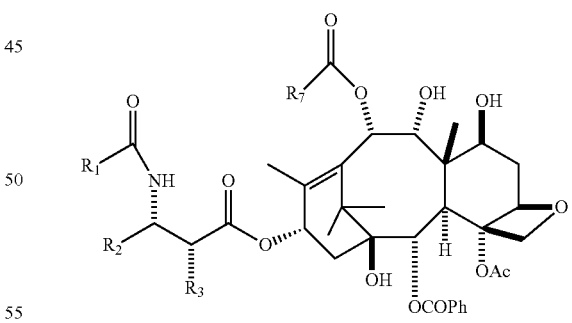

wherein
- $R_1$ and $R_2$ are each selected from H, an alkyl group, an olefinic group, an aromatic group, an O-alkyl group, an O-olefinic group, and an O-aromatic group;
- $R_3$ is hydroxyl or $OP_1$;
- $R_7$=an alkyl group, an olefinic group, or an aromatic group;
- $P_1$ is a hydroxyl protecting group.

The first taxane analog may have a formula selected from the following structures

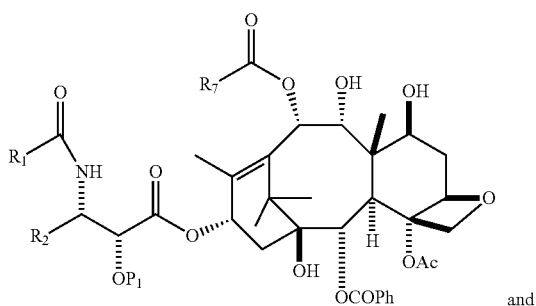

The first taxane analog may then be protected as a 7,9-acetal linked analog to form a second taxane analog of formula

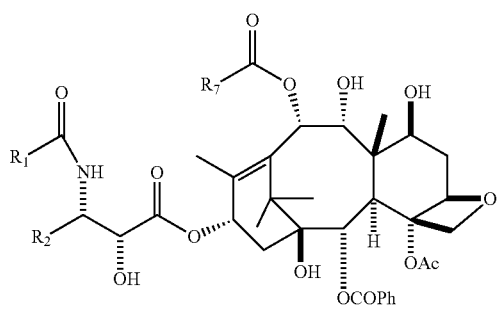

which may specifically have one of the following formulas

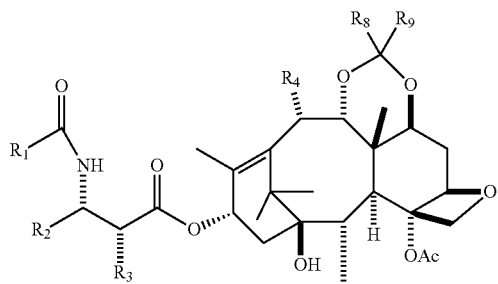

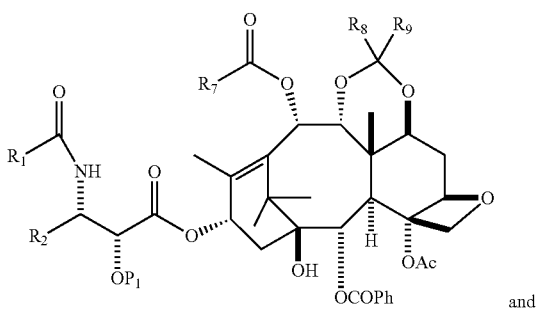

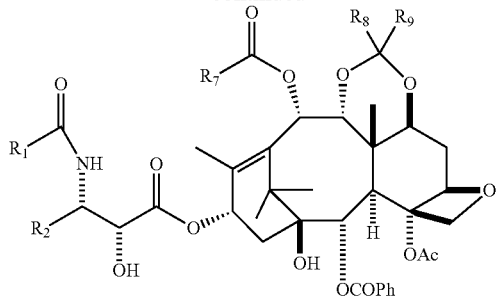

The sidechain of the second taxane analog may thereafter be cleaved at the C-13 position to convert the second taxane analog into a first intermediate compound of formula

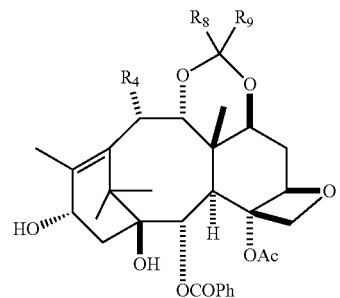

Subsequently, the first intermediate compound may be esterified with a second intermediate compound of formula

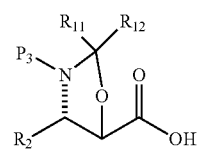

thereby to form a third taxane analog of formula

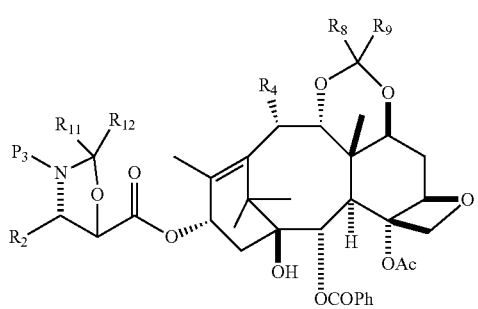

wherein:
  $R_2$ is selected from H, an alkyl group, an olefinic group, an aromatic group, an O-alkyl group, an O-olefinic group, and an O-aromatic group;
  $R_4$ is either hydroxyl or $R_7COO$;
  $R_7$ is an alkyl group, an olefinic group, or an aromatic group;
  $R_8$, $R_9$, $R_{11}$, and $R_{12}$ are each selected from H, an alkyl group, an olefinic group, or an aromatic group; and
  $P_3$ is NH protecting group.

Specifically, the $R_9$ and $R_{12}$ moieties may specifically be

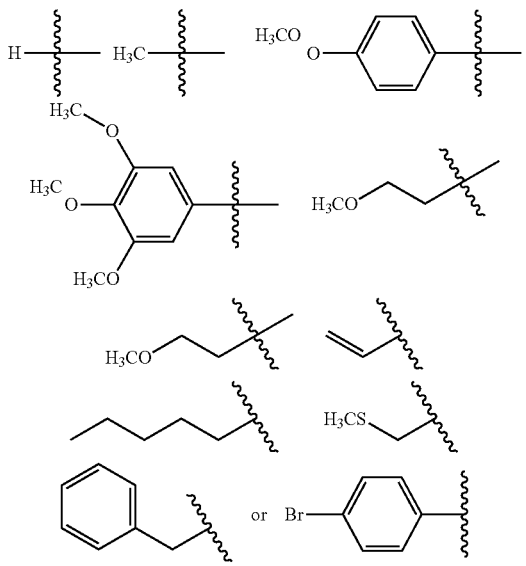

Also, $P_3$ may specifically be carbonbenzyloxy (CBZ).

A further method according to the present invention comprises converting a first compound of formula:

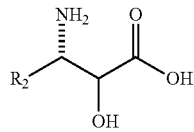

to a second compound of formula:

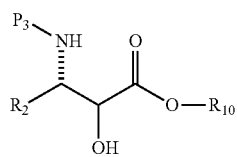

protecting the second compound as an N,O-acetal to form a third compound of formula:

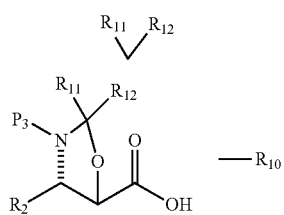

and saponifying the third compound to a fourth compound of formula:
where $R_2$, $R_{11}$, $R_{12}$ and $P_3$ are as defined in Table 1 above and $R_{10}$ is an alkyl group such as a methyl or ethyl group.

Finally, the present invention contemplates a method of treating cancer in a patient, comprising administering to the patient a pharmaceutical formulation including a selected concentration of a taxane and a pharmaceutically acceptable carrier therefor, wherein the taxane has a formula:

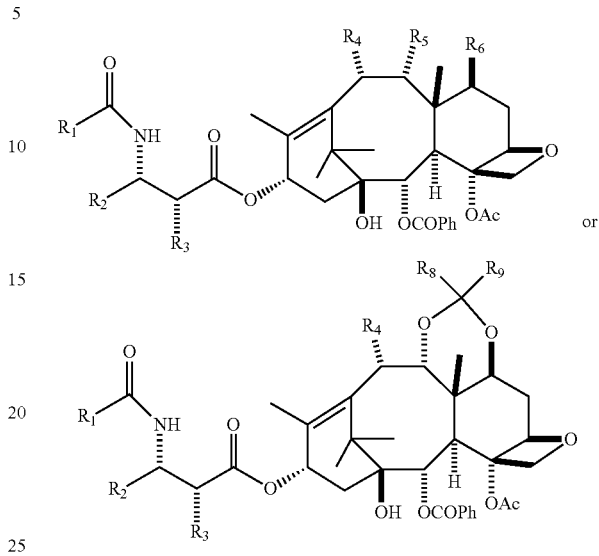

and C-2'S isomers thereof wherein $R_1$ through $R_9$ are as defined in Table 1 above.

These and other objects of the present invention will become more readily appreciated and understood from a consideration of the following detailed description of the exemplary embodiments of the present invention when taken together with the accompanying drawings, in which:

BRIEF DESCRIPTION OF THE DRAWINGS

FIG. 7 is a diagram of a generalized Scheme 5 for forming 9,10-α,α taxane analogs according to the present invention;

FIG. 8 is a diagram of a generalized Scheme 6 for forming 9,10-α,α-7,9-acetal taxane analogs according to the present invention;

DETAILED DESCRIPTION OF THE INVENTION

Figure 1:
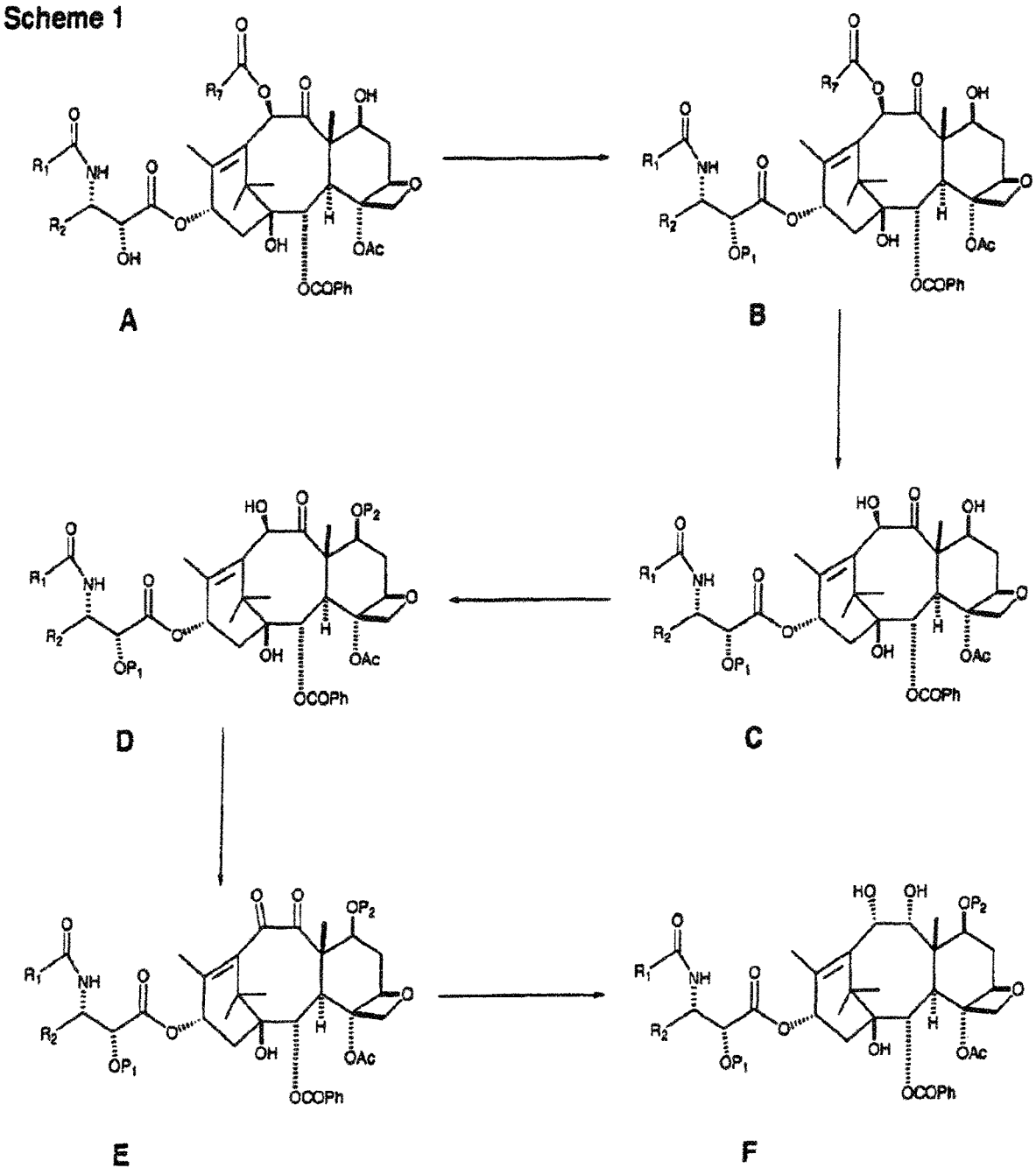
FIG. 1 is a diagram of a generalized Scheme 1 for forming 9,10-α,α taxane analogs according to the present invention.

Paclitaxel and docetaxel have a formula as follows:

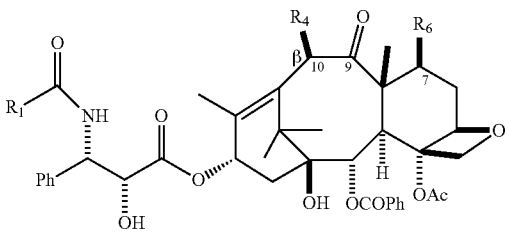

Paclitaxel: $R_1 = Ph, R_4 = AcO$
Docetaxel $R_1 = $ t-Butoxy, $R_4 = OH$

Of note is the top part of the molecule as illustrated above, which may be seen to have a 9-keto structure and 10-β hydroxy or 10β acetyl stereochemistry. The present invention provides novel taxane analogs having a stereochemistry at the C-9 and C-10 OH positions of the molecule. Generally, these compounds have been found to exhibit excellent inhibition of cell growth against MDR sensitive cancer cell lines. For example, the 9,10-α,α hydroxy taxane derivatives discussed in Table 2 exhibit favorable inhibition of cell growth in several of the tested cell lines.

TABLE 2

BIOLOGICAL ACTIVITY DATA OF SELECTED TAXANES

| Cancer Type & Cell line | MDR | Tubulin | Agent | Concentration | Inhibition |
|---|---|---|---|---|---|
| Ovarian Carcinoma 1A9PTX10 | + | Mutant | Paclitaxel | 5 ug/mL | 55% |
| Ovarian Carcinoma 1A9PTX10 | + | Mutant | TPI 287 | 0.2 ug/mL | 85% |
| Ovarian Carcinoma 1A9PTX10 | + | Mutant | TPI 287 | 0.1 ug/mL | 51% |
| Ovarian Carcinoma 1A9PTX10 | + | Mutant | TPI 251 | 0.5 ug/mL | 96% |
| Ovarian Carcinoma 1A9PTX10 | + | Mutant | TPI 251 | 0.25 ug/mL | 93% |
| Breast Cancer MCF-7 NCI-AR | + | Wild Type | Paclitaxel | 40 ug/mL | 55% |
| Breast Cancer MCF-7 NCI-AR | + | Wild Type | TPI 287 | 0.5 ug/mL | 80% |
| Breast Cancer MCF-7 NCI-AR | + | Wild Type | TPI 287 | 0.25 ug/mL | 47% |
| Breast Cancer MCF-7 NCI-AR | + | Wild Type | TPI 287 | 0.125 ug/mL | 37% |
| Breast Cancer MCF-7 NCI-AR | + | Wild Type | TPI 287 | 0.061 ug/mL | 22% |
| Breast Cancer MCF-7 NCI-AR | + | Wild Type | TPI 287 | 0.031 ug/mL | 13% |

TABLE 2-continued

BIOLOGICAL ACTIVITY DATA OF SELECTED TAXANES

| Cancer Type & Cell line | MDR | Tubulin | Agent | Concentration | Inhibition |
|---|---|---|---|---|---|
| Breast Cancer MCF-7 NCI-AR | + | Wild Type | TPI 251 | 2.0 ug/mL | 94% |
| Breast Cancer MCF-7 NCI-AR | + | Wild Type | TPI 251 | 1.0 ug/mL | 65% |
| Breast Cancer MCF-7 NCI-AR | + | Wild Type | TPI 251 | 0.5 ug/mL | 45% |
| Breast Cancer MCF-7 NCI-AR | + | Wild Type | TPI 285 | 2.0 ug/mL | 85% |
| Breast Cancer MCF-7 NCI-AR | + | Wild Type | TPI 285 | 1.0 ug/mL | 51% |
| Breast Cancer MCF-7 NCI-AR | + | Wild Type | TPI 285 | 0.5 ug/mL | 41% |
| Neuroblastoma SK-N-AS | − | Wild Type | Paclitaxel | 0.1 ug/mL | 54% |
| Neuroblastoma SK-N-AS | − | Wild Type | TPI 287 | 0.05 ug/mL | 58% |
| Squamous Cell Carcinoma FADU | − | Wild Type | Paclitaxel | 0.05 ug/mL | 47% |
| Squamous Cell Carcinoma FADU | − | Wild Type | TPI 287 | 0.05 ug/mL | 56% |

Table 2, above, identifies the compounds TPI 287, TPI 285 and TPI 251, which were found to exhibit excellent inhibition of cell growth against MDR sensitive cancer cell lines. The compounds TPI 287, TPI 285 and TPI 251 are discussed in greater detail below and have the following respective structures:

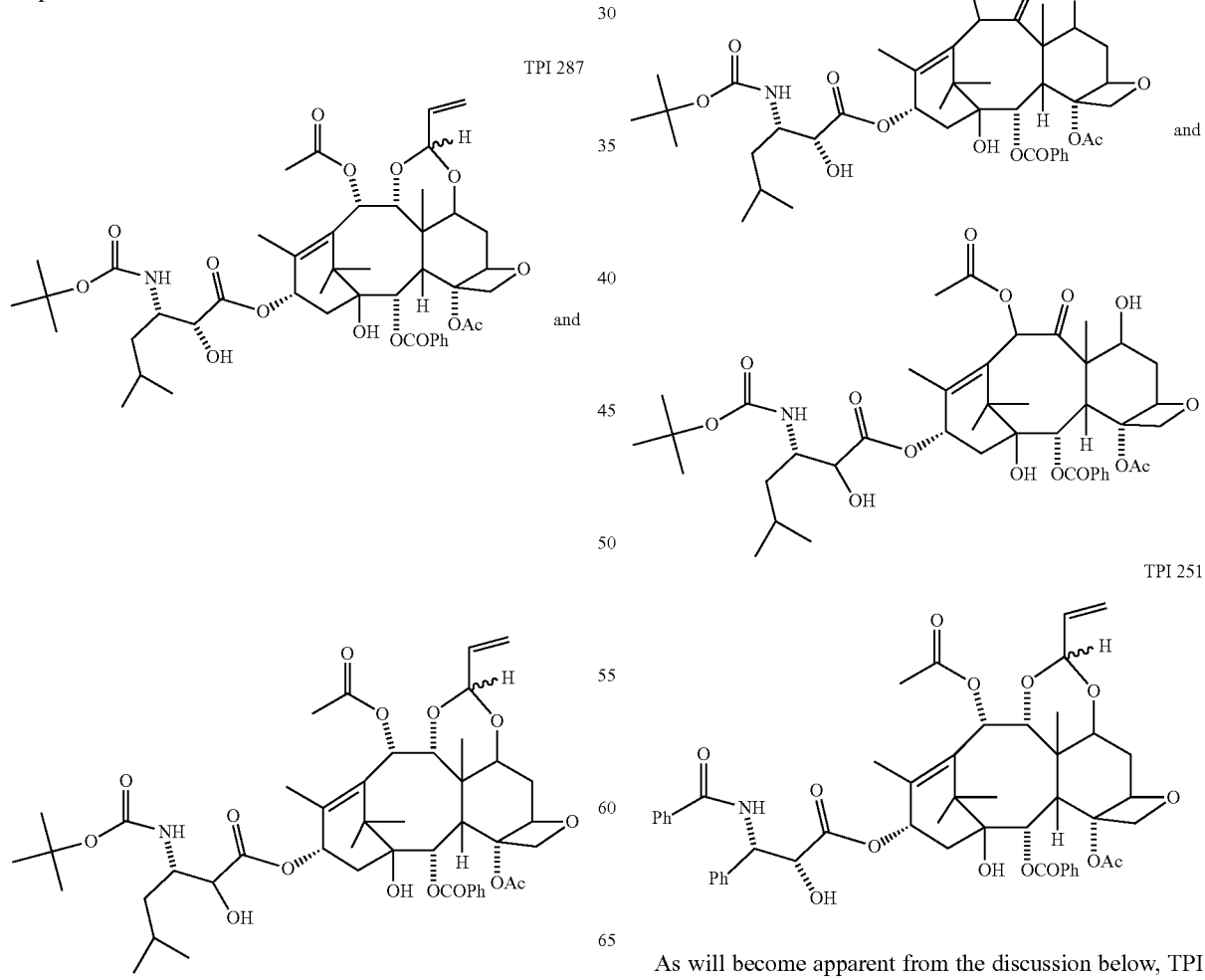

As will become apparent from the discussion below, TPI 287 is a mixture of the compounds identified as Formula 31 and Formula 33, which are discussed below with respect to FIG. 35. The 2'R isomer of TPI 285 is illustrated, for example, with respect to generalized Formula A in FIG. 1 wherein $R_1$ is a tert-butoxyl group, $R_2$ is an isobutyl group and $R_7$ is acetyl. Although not shown in FIG. 1, the 2'S isomer of TPI 285, as shown above, is also contemplated. TPI 251 is illustrated, for example, with respect to generalized Formula Z in FIG. 9 wherein $R_8$ is H and $R_9$ is ethylene. In addition to the compounds TPI 287, TPI 285, and TPI 251, various other 9,10-α,α hydroxy taxane derivatives have also exhibited significant inhibition against various cancer cell lines.

Synthesis of 9,10-α,α-Hydroxy Taxanes

Such compounds may be formed in a number of ways according to the present invention. For example, as shown in FIG. 1 (Scheme 1) and FIG. 2 (Scheme 2), a 9,10-α,α hydroxy taxane F may be formed directly from a standard taxane A or A' through various transformations, including oxidation of a 10-hydroxy taxane D to a 9,10-diketo taxane E and reduction to the 9,10-α,α-hydroxy taxane F. In the compounds shown in Schemes 1 and 2, $R_1$ and $R_2$ may each be H, alkyl such as an isobutyl group or a tert-butyl group, olefinic such as a tigloyl group, aromatic such as a phenyl group, O-alkyl, O-olefinic, or O-aromatic; $R_7$ may be alkyl such as a methyl group, olefinic or aromatic; and $P_1$ and $P_2$ may each be a hydroxyl protecting group, such as a silyl protecting group, including TBDMS or TES.

Figure 13:
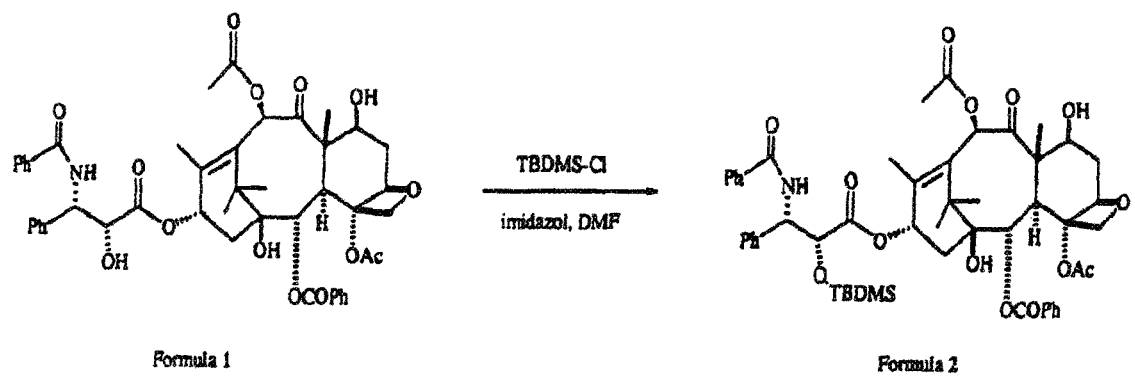
FIG. 13 is a diagram of an exemplary 2'-hydroxyl protection of paclitaxel according to the present invention.

Such a process is exemplified in FIGS. 13 through 17. For example, as shown in FIG. 13, paclitaxel of Formula 1 (where $R_1=R_2=Ph$; $R_7=CH_3$ in generalized formula A of Scheme 1) is first protected at the 2'-hydroxyl with a hydroxyl protecting group such as tert-butyldimethylsilyl (TBDMS). To a 500 mL round bottom flask (RBF) equipped with a magnetic stir bar was charged 50.0 g (58.55 mmol) paclitaxel, Formula 1, 13.96 g (204.8 mmol, 3.5 eq.) imidazole, and 26.47 g (175.7 mmol, 3.0 eq.) TBDMS-Cl. The flask was placed under a nitrogen environment and 350 mL (7 mL/g paclitaxel) anhydrous N,N-dimethyl formamide (DMF) was charged to the flask. The reaction was stirred at room temperature for twenty hours, then was worked up by diluting the reaction solution in 600 mL isopropyl acetate (IPAc) and washing with water until the aqueous wash reached pH 7, then with brine. The organic partition was dried over magnesium sulfate, filtered and then was evaporated to a white foam solid to yield 66.9 g (93.0 area percent) of unpurified 2'-O-TBDMS paclitaxel product of Formula 2 (where $R_1=R_2=Ph$; $R_7=CH_3$; $P_1=TBDMS$ in generalized formula B of Scheme 1). This reaction is nearly quantitative. There are slight amounts of 2',7-bis-TBDMS, but this is not a significant amount.

Figure 14:
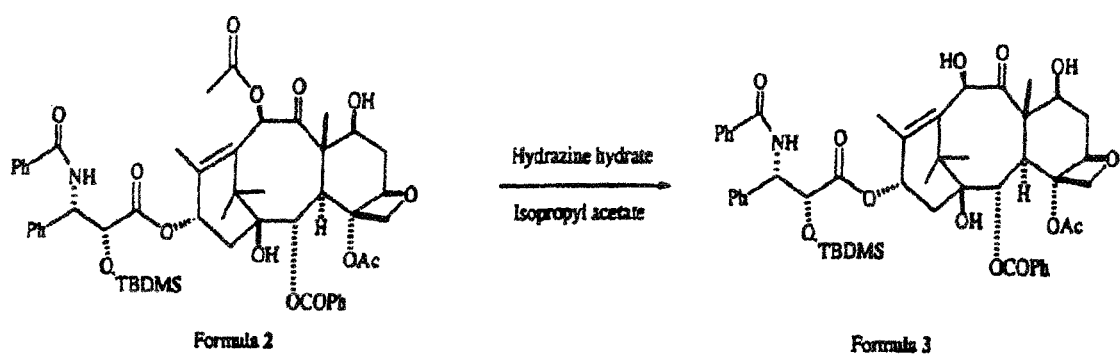
FIG. 14 is a diagram of an exemplary 10-deacylation of the compound formed in FIG. 13.

Next, as shown in FIG. 14, the 10-acetyl group is removed by hydrazinolysis. To a 1 L RBF equipped with a magnetic stir bar was charged 59.5 g 2'-O-TBDMS paclitaxel of Formula 2 and 600 mL (10 mL/g) IPAc. The solution was stirred to dissolve the 2'-O-TBDMS paclitaxel, then 60 mL (1 mUg) hydrazine hydrate was charged to the flask and the reaction stirred at room temperature for one hour. The reaction was worked up by diluting the reaction solution in 1.2 L IPAc and washing first with water, then ammonium chloride solution, then again with water until the aqueous wash was pH 7 and lastly with brine. The organic partition was dried over magnesium sulfate, filtered and evaporated to 55.8 g of solid. The solid was redissolved in 3:1 IPAc (1% water):heptane to a concentration 0.25 g/mL total dissolved solids (TDS) and purified on a YMC silica column; the column eluent was monitored for UV absorbance. The fractions were pooled based on HPLC analysis and evaporated to yield 39.3 g (98.6 area percent) of 2'-O-TBDMS-10-deacetyl paclitaxel solid of Formula 3 (where $R_1=R_2=Ph$; $P_1=TBDMS$ in generalized formula C of Scheme 1). If the reaction goes too long (beyond 2 h), the product begins epimerizing at the C-7 position. Besides decreasing the yield by the formation of the 7-epi degradant, this impurity requires adding a chromatographic step to remove the impurity.

Figure 15:
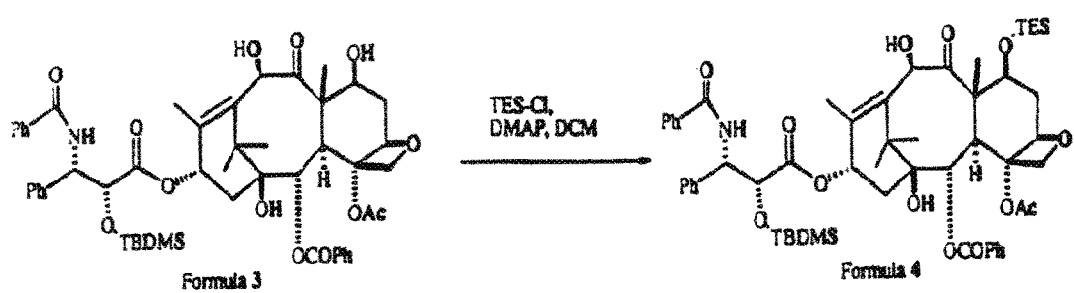
FIG. 15 is a diagram of an exemplary 7-hydroxyl protection of the compound formed in FIG. 14.

As illustrated in FIG. 15, the 7-hydroxyl is now protected with a protecting group such as triethylsilyl (TES). To a 500 mL RBF equipped with a magnetic stir bar was charged 39.3 g (42.46 mmol) 2'-O-TBDMS-10-deacetyl paclitaxel of Formula 3 and 15.6 g (127.4 mmol, 3 eq.) DMAP. The flask was placed under nitrogen and 390 mL (10 mL/g) anhydrous dichloromethane (DCM) charged to the flask to dissolve the solids followed by 14 mL (84.92 mmol, 2 eq.) TES-Cl. The reaction was stirred at room temperature for three hours. The reaction was worked up by evaporating the reaction solution to approximately half its starting volume and diluting it in 300 mL EtOAc and washing with water and dilute HCl solutions until the pH of the aqueous wash was approximately 7, then with brine. The organic partition was dried over magnesium sulfate and evaporated to yield 42.0 g (97.7 area percent) of white solid of Formula 4 (where $R_1=R_2=Ph$; $P_1=TBDMS$; $P_2=TES$ in generalized formula D of Scheme 1). This reaction is nearly quantitative, with a slight amount of 7,10-bis-TES and excess silyl compounds in the worked up solids, as with the 2'-TBDMS protection step above.

Figure 16:
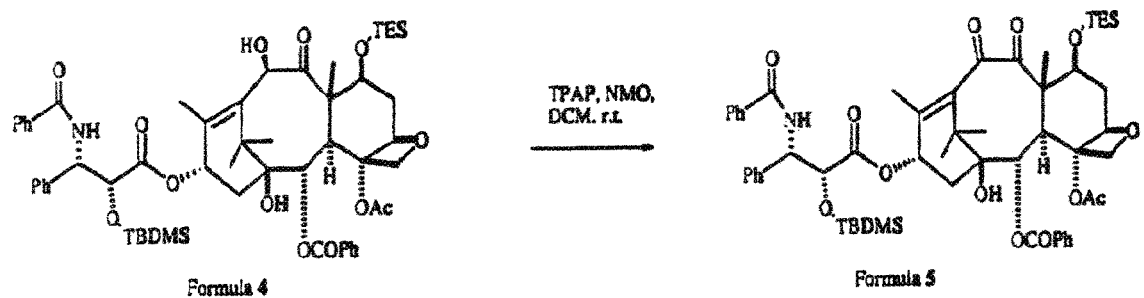
FIG. 16 is a diagram of an exemplary 10-hydroxyl oxidation of the compound formed in FIG. 15.

Next, oxidation of the 10-hydroxyl yields a 9,10-diketo compound, as exemplified in FIG. 16. To a 1 L RBF equipped with a magnetic stir bar was charged 41.0 g (39.43 mmol) 2'-O-TBDMS-7-O-TES-10-deacetyl paclitaxel of Formula 4, 2.1 g (5.92 mmol, 0.15 eq.) of TPAP, 13.9 g (118.3 mmol, 3 eq.) NMO. The flask was placed under nitrogen and 720 mL (~20 mL/g) anhydrous DCM charged to the flask to dissolve the solids. The reaction was stirred at room temperature for 22 hours. The reaction was worked up by concentrating the reaction solution to half its volume and then drying the reaction contents onto 175 g silica gel (EM Sciences 40-634 The taxane containing silica was placed on 30 g of clean silica gel (EM Sciences 40-63µ and the product eluted from the silica with 4 L MTBE. The MTBE was evaporated to yield 37.3 g (93.2 area percent) 2'-O-TBDMS-7-O-TES-9,10-diketo paclitaxel of Formula 5 (where $R_1=R_2=Ph$; $P_1=TBDMS$; $P_2=TES$ in generalized formula E of Scheme 1).

Figure 17:
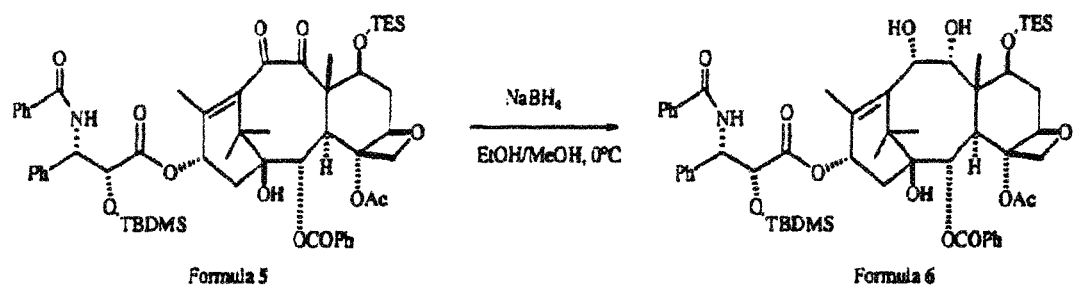
FIG. 17 is a diagram of an exemplary 9,10-diketo reduction of the compound formed in FIG. 16.

Finally, reduction of the 9,10-diketo taxane yields the 9,10-α,α-hydroxy taxane, as shown for example in FIG. 17. To a 2 L RBF equipped with a magnetic stir bar was charged 37.3 g (35.9 mmol) protected 9,10-diketo paclitaxel of Formula 5 and 900 mL (~30 mL/g taxane) of 3:1 EtOH/MeOH. The solution was stirred to dissolve the solids then the flask was placed in an ice/water bath and the solution was stirred for 30 minutes. 8.1 g (215.7 mmol, 6 eq.) of sodium borohydride ($NaBH_4$) was charged to the flask and the reaction stirred in the ice/water bath for five hours. The reaction was worked up by diluting the reaction solution in 1 L IPAc and washing with 4×750 mL water, then with 200 mL brine. The organic partition was dried over magnesium sulfate. The aqueous washes were reextracted with 500 mL IPAc. The organic reextract solution was washed with 100 mL brine then dried over magnesium sulfate and combined with the first organic partition. The IPAc solution was concentrated until solids began precipitating out then heptane was added to the solution to crystallize the protected 9,10-α,α-OH, 9-desoxo, 10-deacetyl paclitaxel product of Formula 6 (where $R_1=R_2=Ph$; $P_1=TBDMS$; $P_2=TES$ in generalized formula F of Scheme 1). The crystallizing solution was placed in a freezer overnight. Three crystallizations were done on the material, the first yielded 4.1 g (95.3 area percent) protected 9,10-α,α-OH, 9-desoxo, 10-deacetyl paclitaxel product, the second yielded 18.3 g (90.9 area percent) product, and the third yielded 2.9 g (81.7 area percent) product. The original work on this reaction employed flash chromatography to purify the product. However, the crystallizations that were performed gave similar purity, by HPLC, to the chromatographed material from earlier work.

Figure 2:
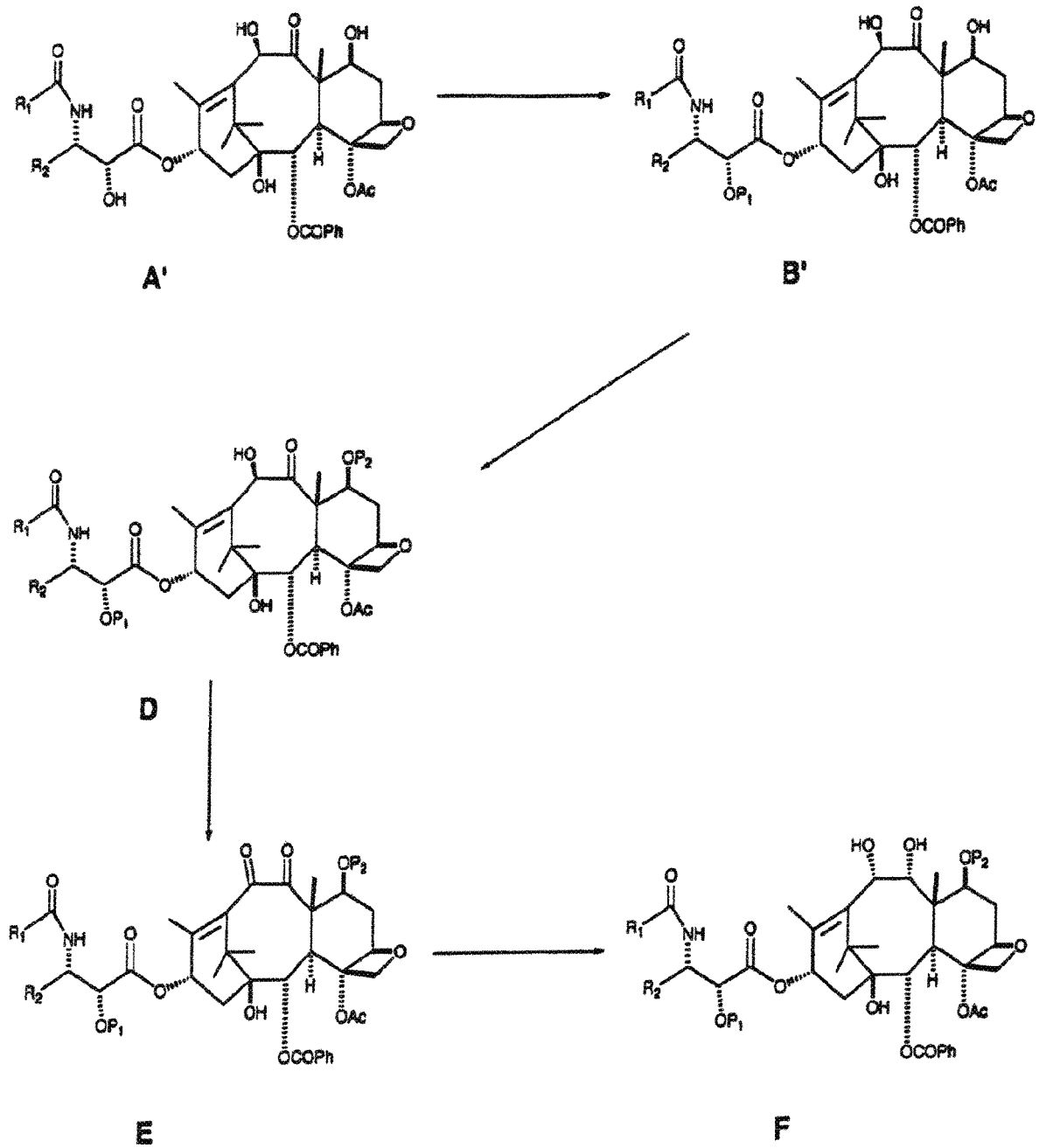
FIG. 2 is a diagram of a generalized Scheme 2 for forming 9,10-α,α taxane analogs according to the present invention.

As illustrated in FIG. 2 (Scheme 2), the same steps as above may be followed—absent the hydrazinolysis step—when the starting material is a 10-deacetyl taxane, such as of generalized Formula A' in FIG. 2.

II. 10-Acylation and 2',7-Deprotection

Figure 3:
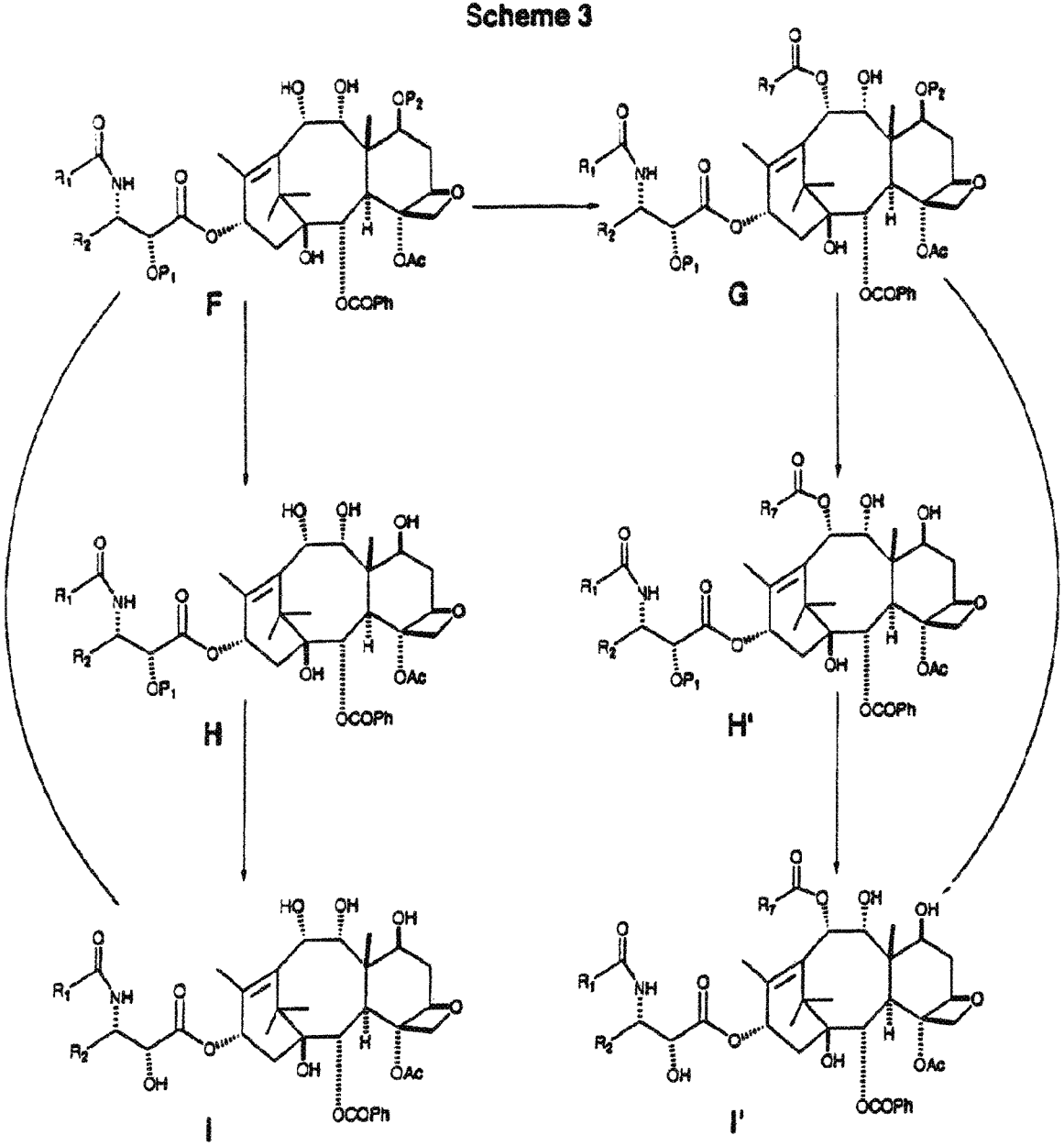
FIG. 3 is a diagram of a generalized Scheme 3 for forming 9,10-α,α taxane analogs according to the present invention.

Next, as shown in FIG. 3 (Scheme 3), the resulting taxane of generalized formula F may be deprotected at the 7-position to yield the taxane of generalized formula H and then deprotected at the 2'-position to yield a taxane of the generalized formula I. The deprotection at the 2'- and 7-positions may be either a two-step process or may be performed in a single step.

Alternatively, as shown in Scheme 3, the taxane of generalized formula F may be first acylated at the 10 position before deprotecting at the 7 and 2' positions. According to this route, the 10 acylation of the taxane of generalized formula F results in the taxane of generalized formula G, which may then be deprotected at 7 position to yield a taxane of the generalized formula H' and deprotected at the 2'-position to yield a taxane of the generalized formula I'. Here again, the deprotection at the 7- and 2'-positions may be either a two-step process or may be performed in a single step.

Figure 18:
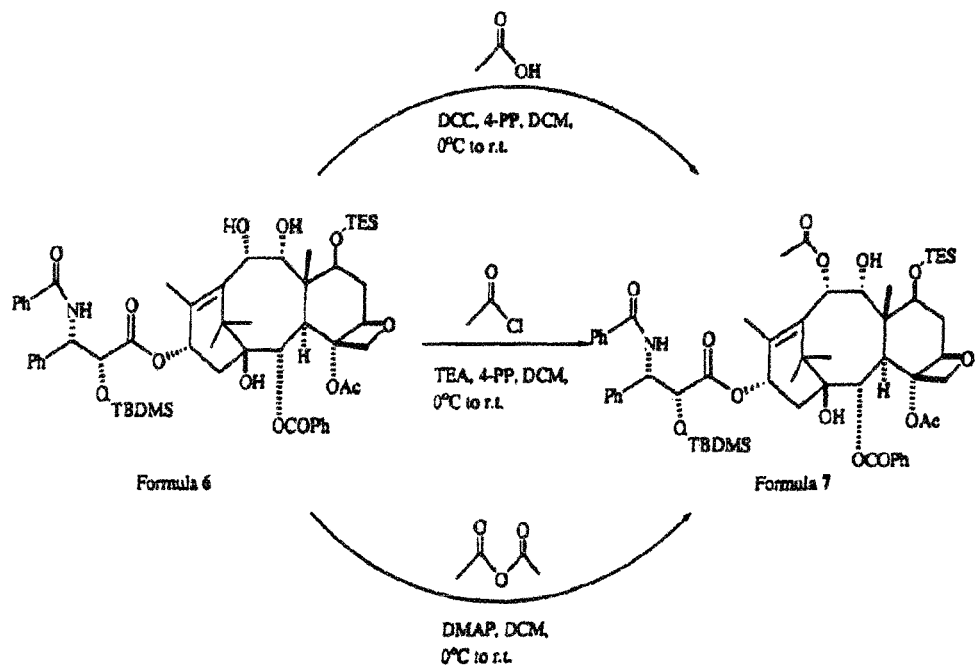
FIG. 18 is a diagram of an exemplary 10-acylation of the compound formed in FIG. 17.

The 10-acylation of the taxane of generalized formula F may be accomplished in a number of manners, as exemplified in FIG. 18. In particular, the invention contemplates the use of either a carboxylic acid of generalized formula $R_7COOH$, a carboxylic acid halide such as an acid chloride of generalized formula $R_7COCl$, or a carboxyl anhydride of generalized formula $R_7COOCOR_7$. In the compounds shown in Scheme 3, $R_1$, $R_2$, $R_7$, $P_1$ and $P_2$ are as defined above for Schemes 1 and 2, although it should be appreciated that the $R_7COO$ group attached at C-10 in Scheme 3 may be different from the $R_7COO$ group that was removed in Scheme 1.

When the reagent used is a carboxylic acid, an exemplary procedure (as shown in FIG. 18) is as follows. To a 25 mL RBF equipped with a magnetic stir bar was charged 300 mg (0.288 mmol) of 2'-O-TBDMS-7-O-TES-9,10-α,α-OH, 9-desoxo, 10 deacetyl paclitaxel of Formula 6 (where $R_1=R_2=Ph$; $P_1=TBDMS$; $P_2=TES$ in generalized formula F of Scheme 3), (0.720 mmol, 2.5 eq.) carboxylic acid ($CH_3COOH$), 178 mg (0.864 mmol, 3.0 eq.) of DCC, and 13 mg (0.086 mmol, 0.3 eq.) of 4-pyrrolidinopyridine (4-Pp). The contents of the flask were placed in a nitrogen environment and 10 mL anhydrous DCM added to the flask. The reactions were stirred at room temperature for 15+ hours (all the reactions were monitored by TLC or HPLC for consumption of the starting material); the reactions generally ran overnight. The reactions were worked up by diluting the reaction solution in 20 mL EtOAc and stirring for fifteen minutes to precipitate dicyclohexyl urea (DCU). The DCU was removed from the solution by vacuum filtration and the filtrate was washed with water until the pH of the water washes was approximately 7. The organic solution was then washed with brine and dried over sodium sulfate before evaporating to dryness.

When the reagent used is a carboxylic acid halide, an exemplary procedure (as shown in FIG. 18) is as follows. To a 25 mL RBF, equipped with a magnetic stir bar and under a nitrogen environment, was charged 300 mg (0.288 mmol) of 2'-O-TBDMS-7-O-TES-9,10-α,α-OH, 9-desoxo 10 deacetyl paclitaxel of Formula 6, (0.720 mmol, 2.5 eq.) acid chloride ($CH_3COCl$), 1404, (1.008 mmol, 3.5 eq.) TEA, 13 mg (0.086 mmol, 0.3 eq.) 4-Pp, and 10 mL anhydrous DCM. The reactions were stirred at room temperature for 15+ hours; reactions generally ran overnight and were monitored by TLC and/or HPLC in the morning for consumption of starting material. The reactions were worked up by diluting the reaction solution in 20 mL EtOAc and washing with water until the pH of the water washes was approximately 7. The organic solution was then washed with brine and dried over sodium sulfate before evaporating to dryness.

When the reagent used is a carboxyl anhydride, an exemplary procedure (as shown in FIG. 18) is as follows. To a 25 mL RBF, equipped with a magnetic stir bar and under a nitrogen environment, was charged 300 mg (0.288 mmol) 2'-O-TBDMS-7-O-TES-9,10-α,α-OH, 9-desoxo 10 deacetyl paclitaxel of Formula 6, (2.880 mmol, 10 eq.) acid anhydride ($CH_3COOCOCH_3$), 106 mg (0.864 mmol, 3 eq.) DMAP, and 5 mL anhydrous DCM. The reactions were stirred at room temperature for 15+ hours. The reactions were worked up by adding 5 mL saturated sodium bicarbonate solution to the reaction flask and stirring for 5 minutes. The solution was then transferred to a seperatory funnel and organics were extracted with 20 mL EtOAc. The organic extract was then washed with saturated sodium bicarbonate and water until the pH of the water washes was approximately 7. The organic partition was then washed with brine and dried over sodium sulfate before evaporating to dryness.

Figure 4:
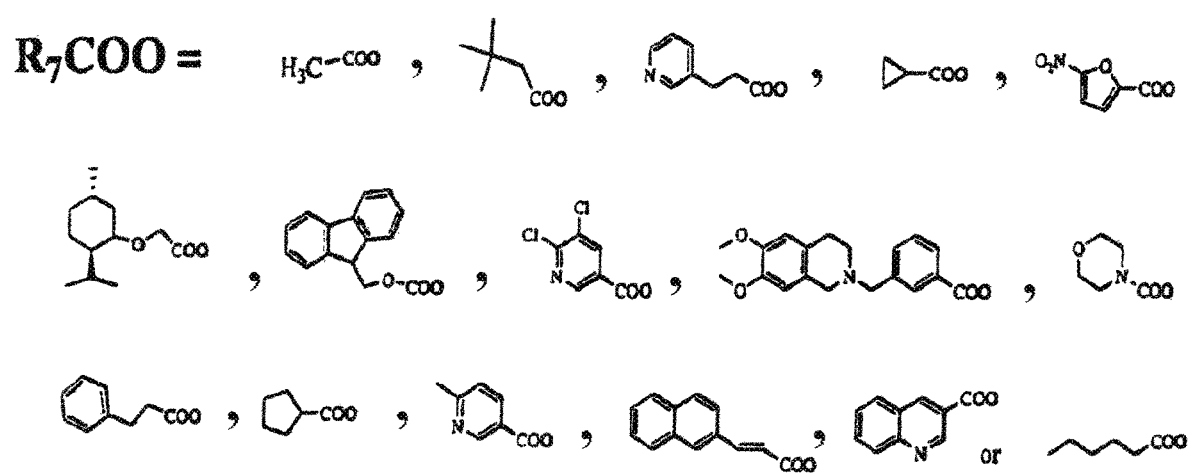
FIG. 4 is a diagram of exemplary $R_7COO$ groups for use in Scheme 3.

The resulting product is the 2'-O-TBDMS-7-O-TES-9-α-OH,9-desoxo,10-epi paclitaxel of Formula 7 (where $R_1=R_2=Ph$; $P_1=TBDMS$; $P_2=TES$; $R_7=CH_3$ in generalized formula G of Scheme 3). FIG. 4 shows numerous alternative groups that may be used for the $R_7COO$ group at the 10-α-position of generalized formula G. As would be appreciated by the ordinarily skilled person, these acylations may be performed for example by substituting the appropriate carboxylic acid $R_7COOH$, carboxylic acid halide $R_7COX$ or carboxyl anhydride $R_7COOCOR_7$ in the above procedures.

Figure 19:
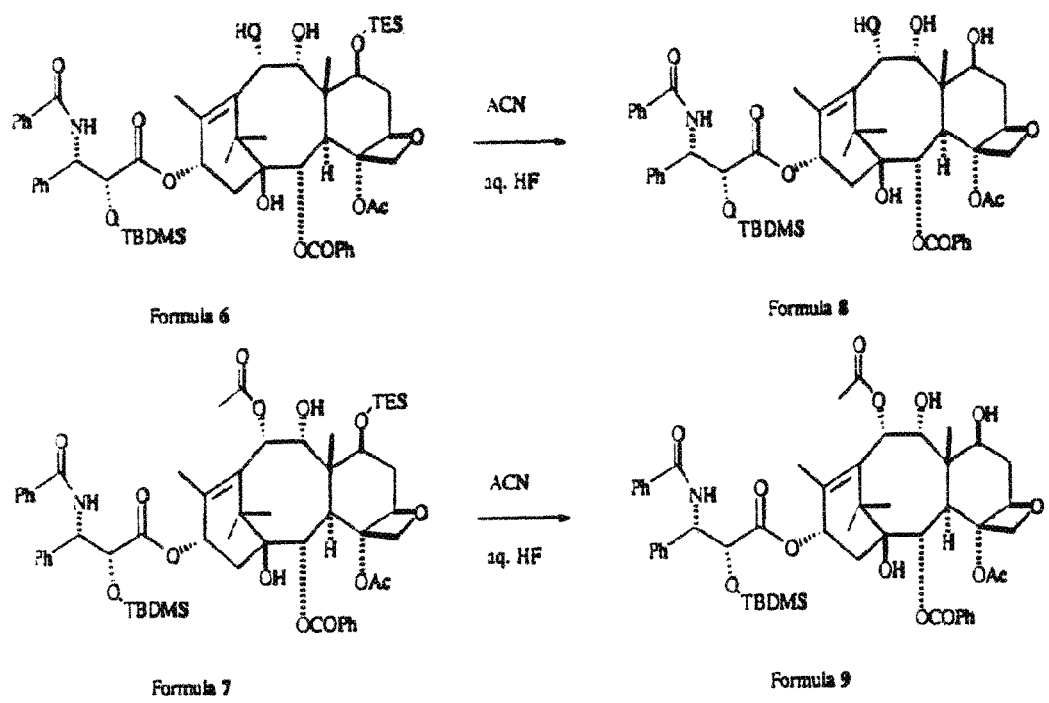
FIG. 19 is a diagram of exemplary 7-deprotections of the compounds formed in FIGS. 17 and 18.
Figure 20:
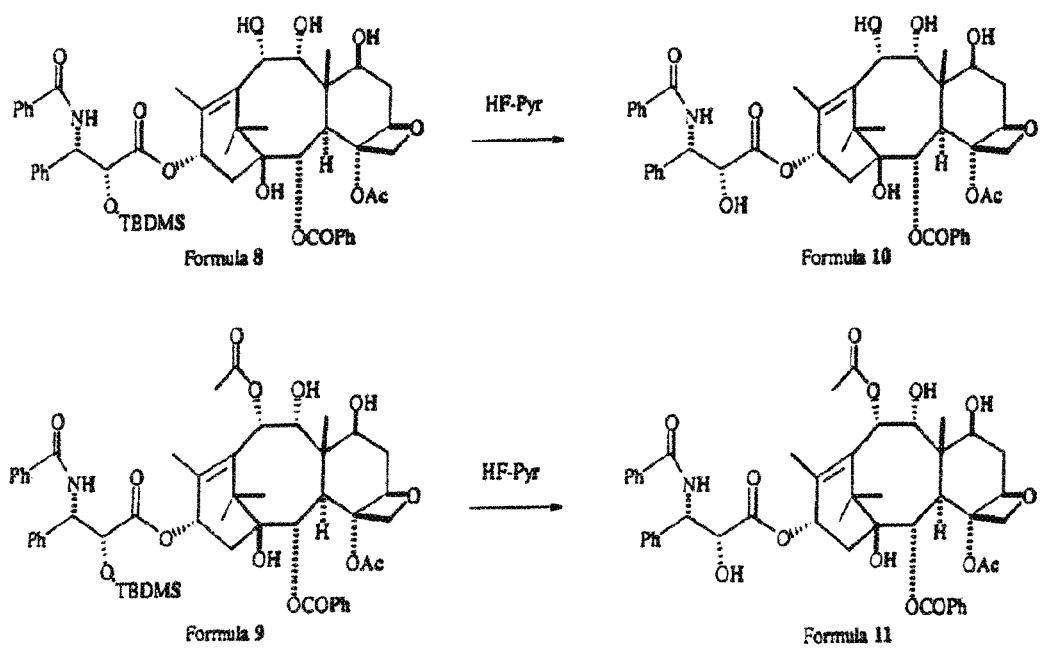
FIG. 20 is a diagram of exemplary 2'-deprotections of the compounds formed in FIG. 19.
Figure 21:
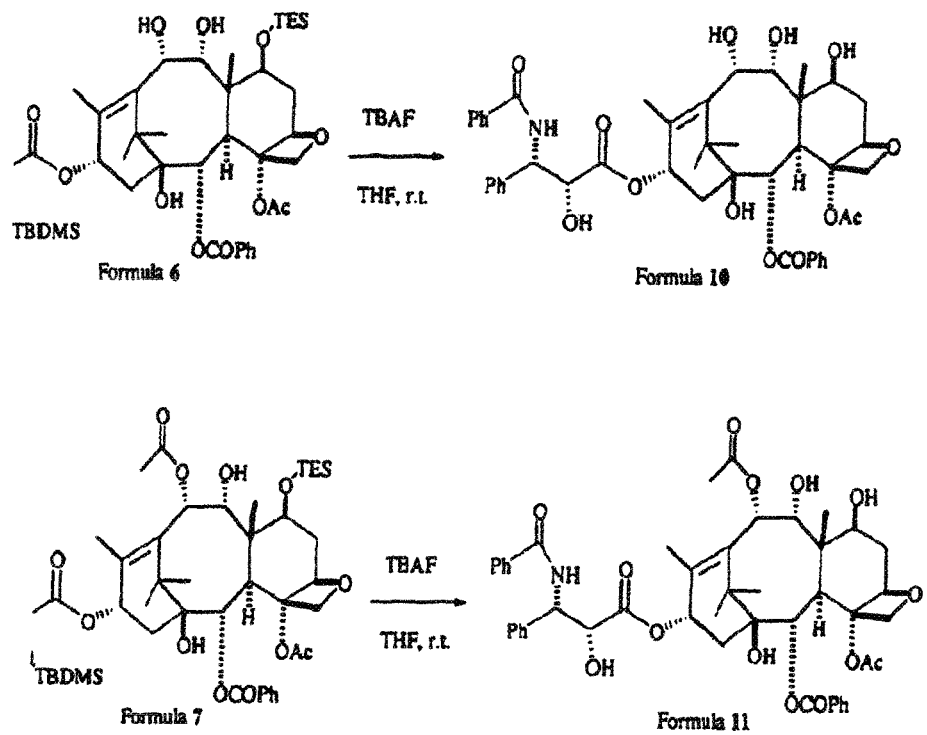
FIG. 21 is a diagram of exemplary 2',7-deprotections of the compounds formed in FIGS. 17 and 18.

As indicated above and as further illustrated in Scheme 3, taxanes of generalized formula F or G may be deprotected at the 2'- and 7-positions in either a two-step process or a single step. FIGS. 19 through 21 show exemplary deprotections of the 2'- and 7-positions.

For example, as shown in FIG. 19, the 7-O-TES group may be removed from Formula 6 to give Formula 8 (where $R_1=R_2=Ph$; $P_1=TBDMS$ in generalized formula H of Scheme 3) or from Formula 7 to give Formula 9 (where $R_1=R_2=Ph$; $P_1=TBDMS$; $R_7=CH_3$ in generalized formula H' of Scheme 3), respectively, using acetonitrile (ACN) and aqueous HF. To a 500 mL teflon bottle equipped with a magnetic stir bar was charged 2.50 g (2.40 mmol) 2'-O-TBDMS-7-O-TES-9,10-α,α-OH, 9-desoxo, 10deacetyl paclitaxel of Formula 6 and 100 mL ACN. The bottle was placed in and ice/water bath and the solution was stirred for 30 minutes. Next, 0.8 mL of 48% HF aqueous was added slowly to the reaction solution and the reaction stirred in the ice/water bath for 20 minutes. The reaction was monitored by TLC for disappearance of the starting material. The reaction was worked up by diluting the reaction solution by adding 200 mL EtOAc and quenching the acid by adding 25 mL saturated sodium bicarbonate solution to the bottle and stirring for 10 minutes. The solution was then transferred to a separatory funnel and the organic partition was washed with water until the pH of the water wash was approximately 7, then was washed with brine. The organic partition was dried over sodium sulfate and then was evaporated to a solid of Formula 8. This procedure was also followed if there was an acyl group on the 10-α-hydroxyl (i.e. Formula 7 to Formula 9 in FIG. 19 or generalized formula G to generalized Formula H' in Scheme 3).

Next, as shown in FIG. 20, the 2'-O-protecting group may be removed from Formula 8 to give Formula 10 (where $R_1$=$R_2$=Ph in generalized formula I of Scheme 3) or from Formula 9 to give Formula 11 (where $R_1$=$R_2$=Ph; $R_7$=$CH_3$ in generalized formula I' of Scheme 3), respectively. To a 50 mL teflon bottle equipped with a magnetic stir bar was charged, 500 mg 2'-O-TBDMS-9,10-α,α-OH, 9-desoxo, 10-deacetyl paclitaxel of Formula 8 (or 2'-O-TBDMS-9-α-OH, 9-desoxo, 10-epi paclitaxel of Formula 9) and 5 mL anhydrous THF. Next, 1 mL HF-pyridine solution was slowly charged to the reaction solution. The reaction was stirred at room temperature for 1 hour; reaction progress was monitored by TLC and/or HPLC for disappearance of starting material. The reaction was worked up by adding 10 mL EtOAc to the bottle to dilute the reaction solution then saturated sodium bicarbonate was slowly added to the bottle to neutralize the HF. The solution was then transferred to a separatory funnel and the organic partition was washed with 10 wt % sodium bicarbonate solution then water until the pH of the water wash was approximately 7. Then the organic partition was washed with brine and then dried over sodium sulfate before evaporating to a solid of Formula 10 (or Formula 11).

It should be appreciated that one ordinarily skilled in the art would understand that the order of the above deprotection steps may be reversed, such that the 2'-hydroxyl protecting group is removed first, and the 7-hydroxyl protecting group removed second.

Further, as indicated above, the 2'- and 7-positions of either the taxanes of the generalized formula F or G may be deprotected in a one-step procedure using tetrabutylammoniumfluoride (TBAF). Here, as shown for example in FIG. 21, Formula 6 may be deprotected directly to Formula 10, and Formula 7 may be deprotected directly to Formula 11. A 10 mL RBF equipped with a magnetic stir bar was charged with 100 mg of 2'-O-TBDMS-7-O-TES-9,10-α,α-OH, 9-desoxo 10 deacetyl paclitaxel of Formula 6 (or 2'-O-TBDMS-7-O-TES-9-α-OH-10-epi paclitaxel of Formula 7) and 5 mL EtOAc or THF to dissolve the taxane. Next, 100 µL of 1M TBAF in THF was charged to the flask and the reaction was stirred at room temperature for 1 hour; the reaction was monitored by TLC and/or HPLC for disappearance of starting material. The reaction was worked up by washing the reaction solution with water and then brine. The organic partition was dried over sodium sulfate and evaporated to a solid of Formula 10 (or Formula 11). This method removes both the 2'-O-TBDMS protecting group and the 7-O-TES protecting group.

III. 7,9,10-Acylation

Figure 5:
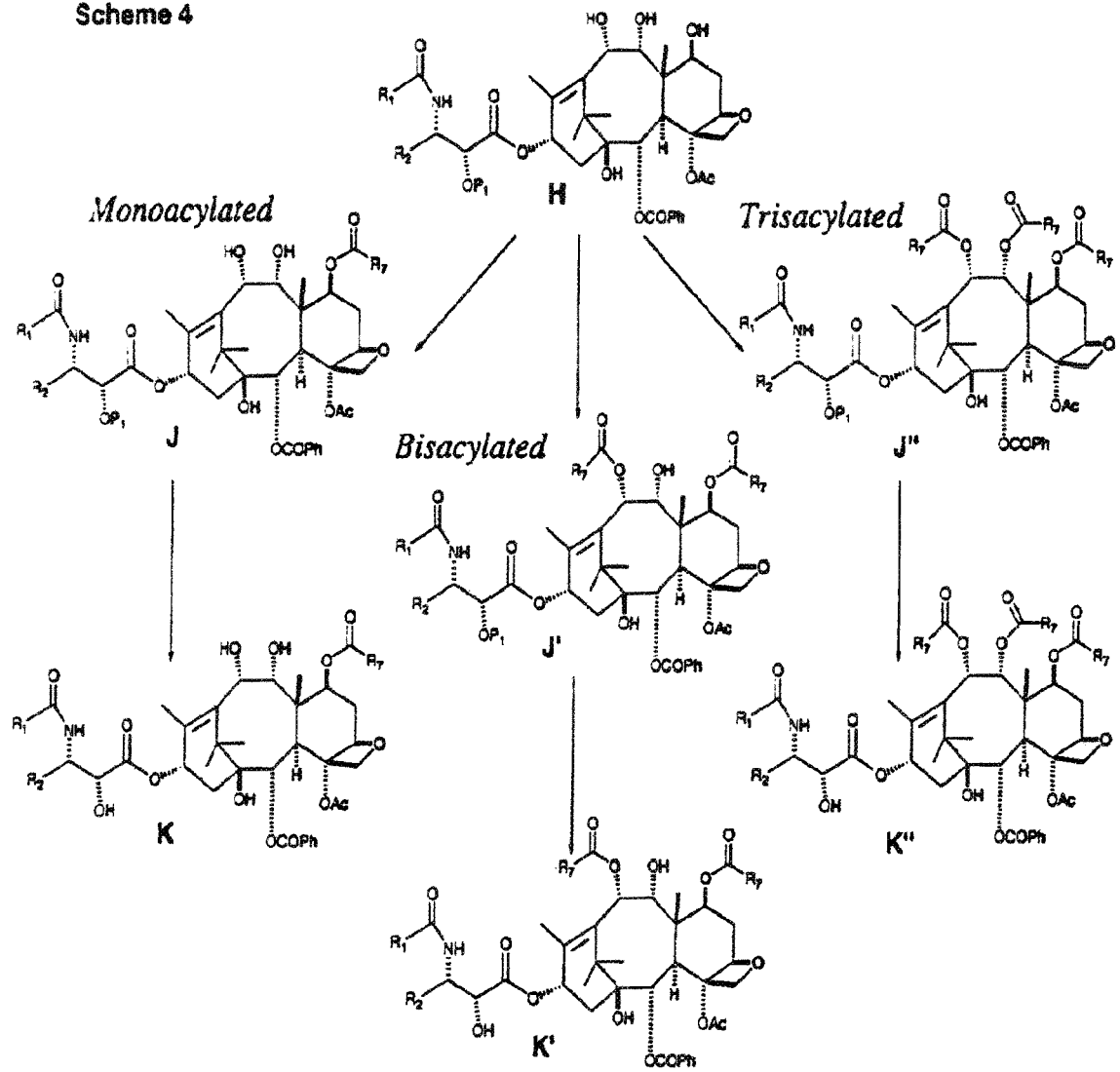
FIG. 5 is a diagram of a generalized Scheme 4 for forming mono-, bis- and tris-acylated 9,10-α,α taxane analogs according to the present invention.
Figure 6:
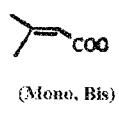
FIG. 6 is a diagram of exemplary $R_7COO$ groups for use in Scheme 4.
Figure 6:
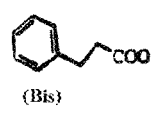
Figure 6:
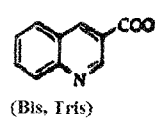
Figure 6:
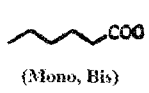
Figure 6:
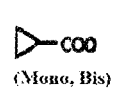
Figure 6:
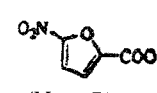
Figure 6:
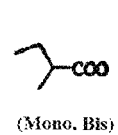
Figure 6:
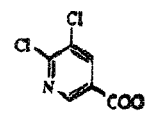
Figure 6:
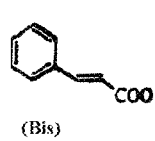
Figure 6:
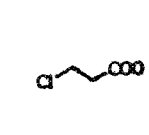
Figure 6:
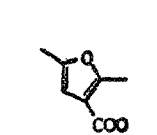
Figure 6:
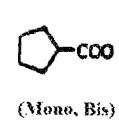
Figure 6:
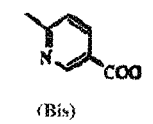
Figure 22:
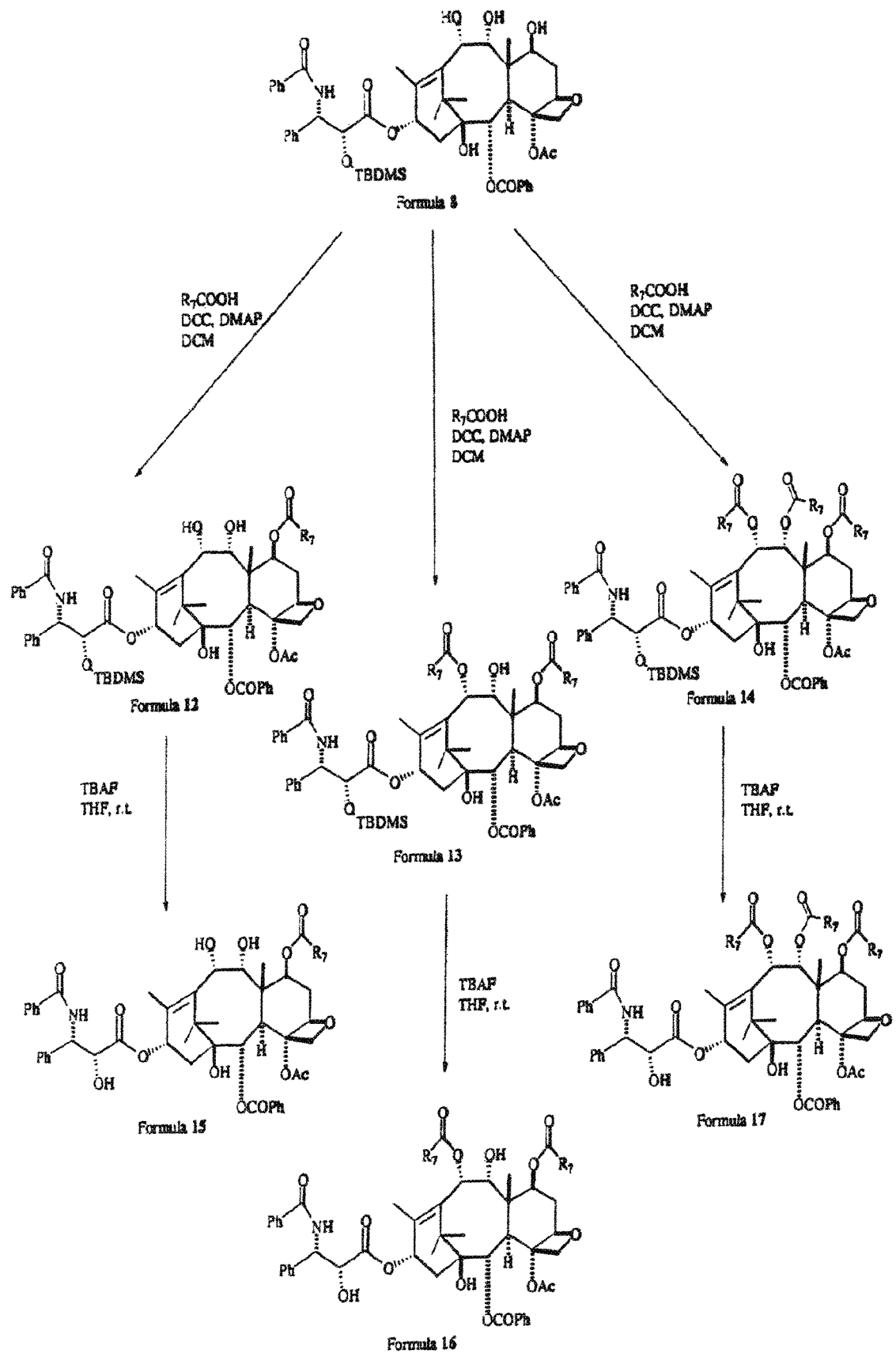
FIG. 22 is a diagram of exemplary mono-, bis- and tris-acylations of a compound formed in FIG. 19, where $R_7COO$ may be selected from the formulas of FIG. 6.

Now, as illustrated in FIG. 5 (Scheme 4), the 7-, 9-, and/or 10-positions may be acylated with various groups $R_7$COO, such as those shown in FIG. 6. In the compounds shown in Scheme 4, $R_1$, $R_2$, $R_7$, and $P_1$ are as defined above for Schemes 1 and 2, although it should be appreciated that the $R_7$COO groups in Scheme 4 may be different from the $R_7$COO group that was removed in Scheme 1. For example, as shown in FIG. 22, 2'-O-TBDMS-9,10-α,α-OH, 9 desoxo, 10 deacetyl paclitaxel of Formula 8 (where $R_1$=$R_2$=Ph; $P_1$=TBDMS in generalized formula H of Scheme 4) may be mono-acylated on the 7-hydroxyl as Formula 12 (corresponding to generalized formula J of Scheme 4), bis-acylated on the 7,10-hydroxyls as Formula 13 (corresponding to generalized formula J' of Scheme 4), and/or tris-acylated on the 7,9,10-hydroxyls as Formula 14 (corresponding to generalized formula J" of Scheme 4). It should be appreciated by the ordinarily skilled person that the appropriate carboxylic acid $R_7$COOH corresponding to the desired $R_7$COO group may be substituted in the procedure below, such as those groups from FIG. 6 or other groups as desired. To a 5 mL RBF, equipped with a magnetic stir bar and nitrogen purge, was charged 100 mg (0.108 mmol) 2'-O-TBDMS-9, 10-α,α-OH, 9 desoxo, 10 deacetyl paclitaxel of Formula 8, (0.324 mmol, 3 eq.) carboxylic acid, 66.8 mg (0.324 mmol, 3 eq.) DCC, 6.6 mg (0.054 mmol, 0.5 eq.) DMAP, and 1.5 mL anhydrous DCM. The reaction was stirred at room temperature for 2.5 hours. The reaction progression was monitored by TLC and/or HPLC. If no acyl addition was detected, an additional charge of reagents was done to try and start the reaction. The reaction produces a mixture of monoacylated, bisacylated, and some trisacylated products. The reaction was worked up by filtering the reaction solution through a 0.2 µm nylon acrodisc. To the filtrate plus a 1 mL DCM wash of the solids 100 mg of IRC-50 ion-exchange resin was added. The mixture was stirred at room temperature for 30 minutes. The mixture was filtered again through a second 0.2 µm nylon acrodisc. As further shown in FIG. 22, the resulting filtrate solution went directly to the reaction to remove the TBDMS from the 2'-hydroxyl using the TBAF method, described above to obtain formula 10 and formula 11 from formula 6 and formula 7 respectively; 150 µL of the reagent was added directly to the filtrate and stirred at room temperature for four hours. The work-up was the same as described above for the deprotection method. Compounds were purified on a reverse phase semi-prep scale HPLC column to provide Formula 15 (corresponding to generalized formula K of Scheme 4), Formula 16 (corresponding to generalized formula K' of Scheme 4) and Formula 17 (corresponding to generalized formula K" of Scheme 4).

IV. 7-Ether Functionality

Figure 23:
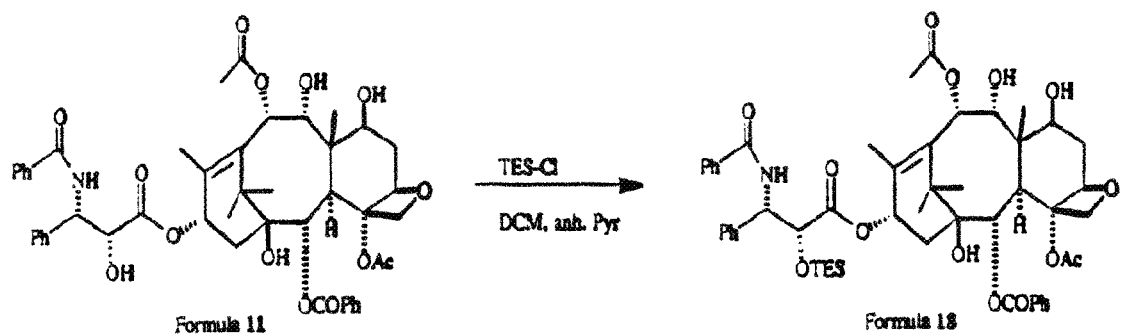
FIG. 23 is a diagram of an exemplary 2'-protection of a compound formed in FIGS. 20 and 21.
Figure 24:
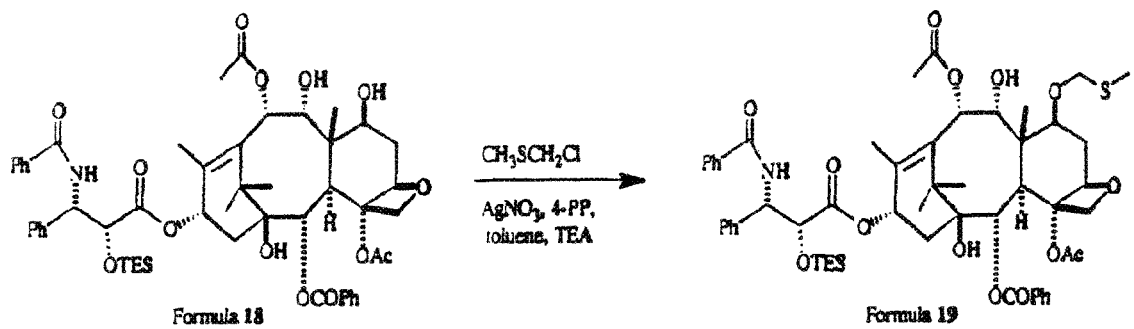
FIG. 24 is a diagram of an exemplary 7-O-methylthiomethylation of the compound formed in FIG. 23.
Figure 25:
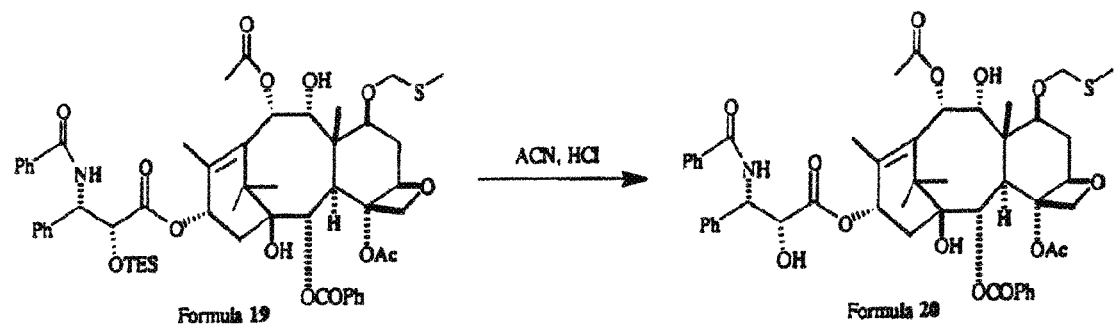
FIG. 25 is a diagram of an exemplary 2-deprotection of the compound formed in FIG. 24.

As illustrated in FIG. 7 (Scheme 5) the 2'-hydroxyl may be protected and a functional group attached at the C-7 position, as shown for example in FIGS. 23 through 25. In the compounds shown in Scheme 5, $R_1$, $R_2$, $R_7$, and $P_1$ are as defined above for Scheme 3, and $R_6$ is an ether functionality, such as an O-methylthiomethyl group or other hetero substituted ether functionalities. Initial attempts to synthesize a 7-O-methylthiomethyl compound from 2'-O-TBDMS-9-α-OH-10-epi paclitaxel provided difficulty in that the methylthiomethyl group was too labile to withstand the 2'-hydroxyl deprotection step using either the HF-pyridine method or the TBAF method, described above. Accordingly, it is desirable to use a 2'-hydroxyl protecting group that can be removed under less harsh conditions, such as a TES protecting group. In FIG. 23, 9-α-OH-10-epi paclitaxel of Formula 11, which may be formed according to one of the routes described above with respect to Scheme 3, is first protected as the 2'-O-TES ether of Formula 18 (where $R_1=R_2=Ph$; $P_1=TES$; $R_7=CH_3$ in generalized formula L of Scheme 5). To a 25 mL RBF, equipped with a magnetic stir bar and a nitrogen purge, was charged 1.2 g (1.415 mmol) 9-α-OH-10-epi paclitaxel of Formula 11, 6 mL anhydrous DCM, and 6 mL anhydrous pyridine. The flask was placed in an ice/water bath and the solution was stirred for 15 minutes. After the solution cooled, 0.95 mL (5.659 mmol, 4.0 eq.) TES-Cl was charged to the flask. The reaction was stirred in the ice/water bath for 3 hours. The reaction was worked up by diluting the reaction solution in 30 mL EtOAc and washing with water then brine. The organic partition was dried over sodium sulfate before evaporating to a solid. The 2'-O-TES-9-α-OH-10-epi paclitaxel product of Formula 18 was purified by flash chromatography using an EtOAc/heptane gradient.

As shown for example in FIG. 24, a methylthiomethyl group may be attached at the 7-O-position to give Formula 19 (where $R_1=R_2=Ph$; $P_1=TES$; $R_7=CH_3$; $R_6=OCH_2SCH_3$ in generalized formula M of Scheme 5). Because the C-9 hydroxyl is very susceptible to oxidation, it is preferred that there are no oxidizing reagents present in the reaction to add the methylthiomethyl ether to the modified taxane. A 100 mL RBF was equipped with a magnetic stir bar, a nitrogen purge, and a condenser, and was wrapped with aluminum foil. 850 mg (0.877 mmol) 2'-O-TES-9-α-OH-10-epi paclitaxel of Formula 18, 894 mg (5.261 mmol, 6 eq.) silver nitrate, 156 mg (1.052 mmol, 1.2 eq.) 4-Pp, 50 mL anhydrous toluene, and 0.8 mL (5.701 mmol, 6.5 eq.) TEA were charged to the flask. The solution was stirred to dissolve the solids then 441 μL (5.261 mmol, 6.0 eq.) chloromethylmethyl-sulfide was charged to the flask. The reaction was heated to 70° C. The reaction was stirred at 70° C. for 24 hours. The reaction was worked up by filtering the reaction solution through Celite. The reaction flask and solids were washed with 80 mL EtOAc. The combined filtrate was transferred to a separatory funnel and washed with water then dilute ammonium chloride then dilute sodium bicarbonate then with water until the pH of the water wash was approximately 7. Next the organic partition was washed with brine then dried over sodium sulfate before it was concentrated to approximately 5 mL. This solution was purified by flash chromatography using an EtOAc/heptane gradient. The fraction pools were evaporated to yield 0.13 g of 2'-O-TES-7-O-methylthiomethyl-9-α-OH-10-epi paclitaxel of Formula 19.

The 2'-hydroxyl is then deprotected, as shown for example in FIG. 25 to provide Formula 20 (where $R_1=R_2=Ph$; $R_7=CH_3$; $R_6=OCH_2SCH_3$ in generalized formula N of Scheme 5). To a 10 mL RBF, equipped with a magnetic stir bar, 0.12 g (0.117 mmol) 2'-O-TES-7-O-methylthiomethyl-9-α-OH-10-epi paclitaxel of Formula 19 and 8 mL ACN were charged. The flask was placed in an ice/water bath and the solution stirred for 30 minutes. 233 (0.233 mmol, 2 eq.) of 1N HCl was charged to the flask and the reaction stirred in the ice/water bath for 45 minutes. The methylthiomethyl ether is fairly acid labile, and the methylthiomethyl group may be removed if the reaction to remove the TES group using 1N HCl in ACN runs too long. The reaction was worked up by pouring the reaction solution into a separatory funnel containing 20 mL EtOAc and 30 mL saturated sodium bicarbonate solution. After agitation the aqueous partition was removed and the organic partition was washed with water until the pH of the water wash was approximately 7 then with brine. The organic partition was dried over sodium sulfate then evaporated to a yellowish oil. The product was purified by reverse phase semi-prep scale HPLC to yield 50 mg of 7-O-methylthiomethyl-9-α-OH-10-epi paclitaxel of Formula 20 as a white solid.

V. 7,9-Acetal Linked Analogs

Figure 9:
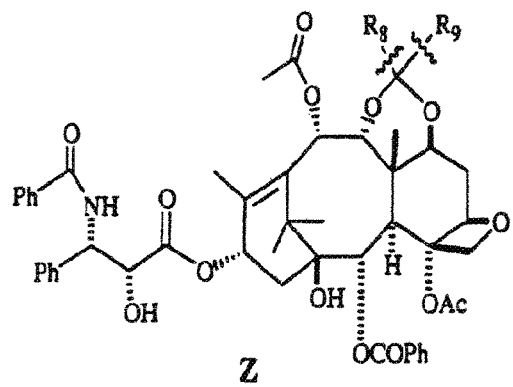
FIG. 9 is a diagram of exemplary compounds formed according to Scheme 6.

As illustrated in FIG. 8 (Scheme 6) the present invention also provides 7,9 acetal linked analogs of 9,10-α,α OH taxanes. In particular, the 7- and 9-positions may be linked through a generalized —OC($R_8$)($R_9$)O— structure and the 2'-position may be deprotected. In the compounds shown in Scheme 6, $R_1$, $R_2$, $R_7$ and $P_1$ are as defined above for Scheme 3, and $R_8$ and $R_9$ may each be H, alkyl, olefinic or aromatic. FIG. 9 illustrates various 7,9-acetal linked analogs of formula Z formed according to the method described below. Initial data from a cytotoxicity study on the compound where $R_8=R_9=H$ in FIG. 9 suggested that there was good activity for the acetal. It should be appreciated that the present invention contemplates further variations in the substituents of such 7,9-acetal linked analogs. For example, the $R_8$ and $R_9$ groups shown in FIG. 9, or others, may be substituted for $R_8$ and $R_9$ in the generalized formulas O and P of Scheme 6, and the $R_1$, $R_2$, $R_7$ and $P_1$ groups thereof may be further varied as described herein.

Figure 26:
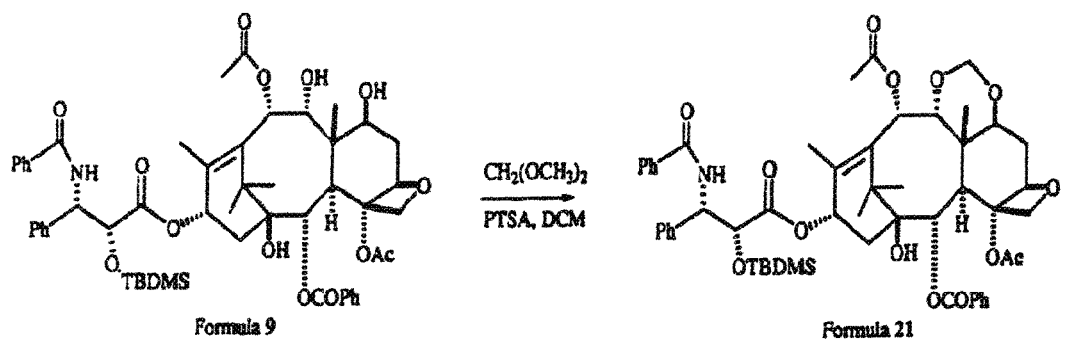
FIG. 26 is a diagram of an exemplary 7,9-acetalization reaction of a compound formed in FIG. 19.
Figure 27:
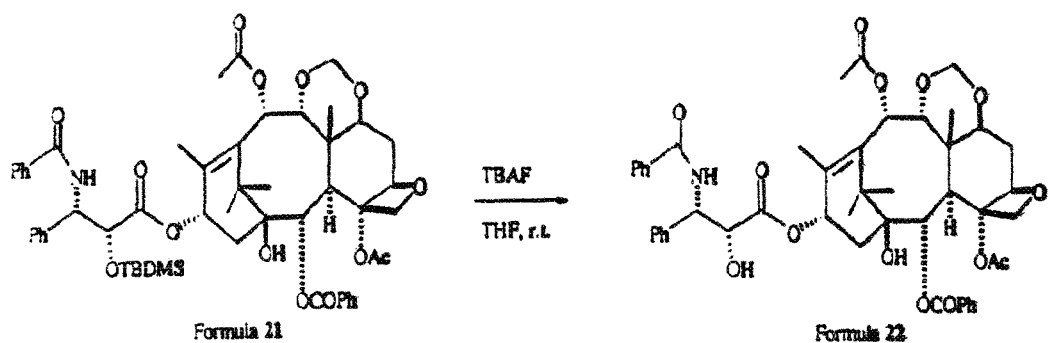
FIG. 27 is a diagram of an exemplary 2'-deprotection of the compound formed in FIG. 26.

For example, as shown in FIG. 26, a compound of Formula 9 (which may be formed as described above with respect to FIG. 19) may be protected as a 7,9-acetal linked analog of Formula 21 (where $R_1=R_2=Ph$; $P_1=TBDMS$; $R_7=CH_3$; $R_8=R_9=H$ in generalized formula O of Scheme 6). To a 10 mL RBF, equipped with a magnetic stir bar and nitrogen purge, 100 mg (0.103 mmol) 2'-O-TBDMS-9-α-OH-10-epi paclitaxel of Formula 9, 2.5 mg (0.013 mmol, 0.13 eq.) p-toluene sulfonic acid, and 5 mL anhydrous DCM were added. The solution was stirred to dissolve the solids then $CH_2(OCH_3)_2$ (0.515 mmol, Seq.) was added and the reaction was stirred at room temperature for 1.5 hours. Reaction progress was monitored by TLC and/or HPLC. The reaction was worked up by diluting the reaction solution in 10 mL and washing the resulting solution with water then brine. The organic partition was dried over sodium sulfate and evaporated to a solid of Formula 21. The protected product was purified on a reverse phase semi-prep scale HPLC before running the TBAF deprotection method, as shown in FIG. 27, to remove the TBDMS group to form Formula 22 (where $R_1=R_2=Ph$; $R_7=CH_3$; $R_8=R_9=H$ in generalized formula O of Scheme 6). As apparent from Scheme 6, it should be appreciated that compounds of generalized formula $R_8R_9C(OCH_3)_2$ may be substituted in the reaction above to provide 7,9-acetal linked analogs having $R_8$ and $R_9$ groups, such as those illustrated in FIG. 9 or others.

VI. Replacement of Taxane Sidechain

Figure 10:
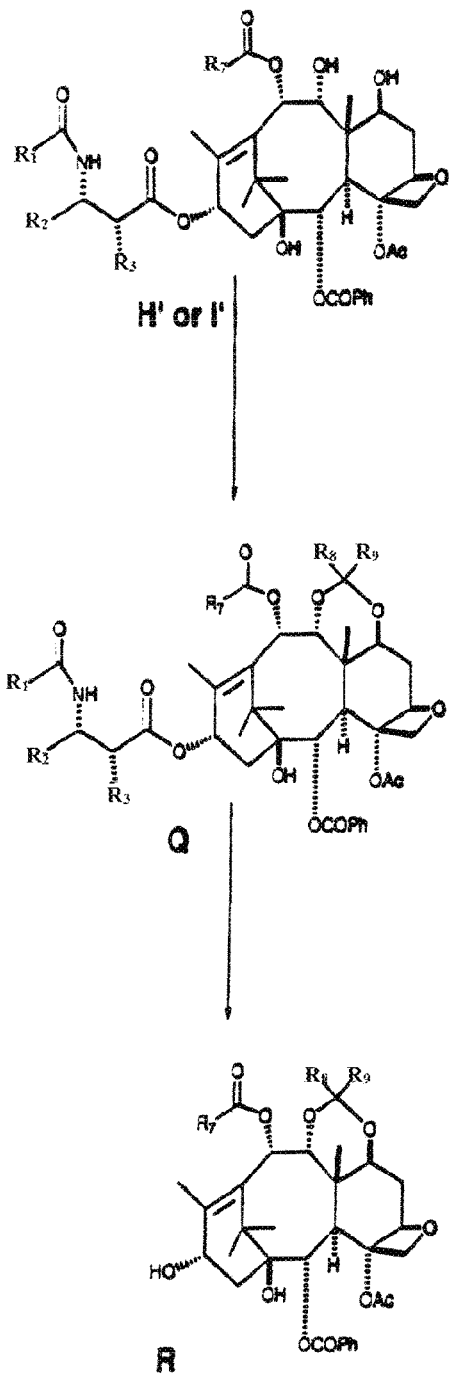
FIG. 10 is a diagram of a generalized Scheme 7 for cleaving the sidechain of 9,10-α, α taxane analogs according to the present invention.
Figure 12:
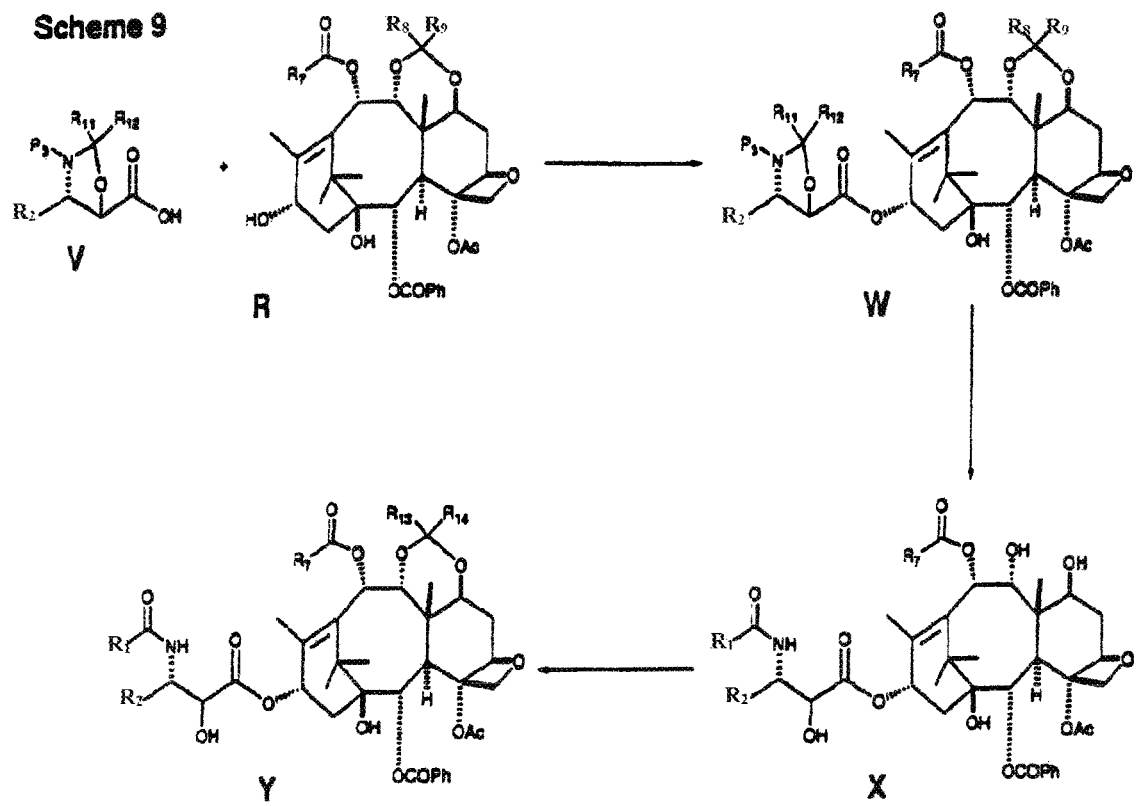
FIG. 12 is a diagram of a generalized Scheme 9 for esterifying the sidechain of FIG. 11 to a 13-hydroxy-9,10-α,α taxane analog according to the present invention.

The discussion above and the corresponding figures illustrate various methods of producing 9,10-α,α-OH taxanes as well as intermediate compounds useful in the formation of those taxanes. With respect to those 9,10-α,α-OH taxanes produced by those methods, the sidechain may be cleaved therefrom so as to attach an alternative sidechain having different substituents than those shown and described. Accordingly, FIG. 10 provides a generalized Scheme 7 for cleaving the sidechain of 9,10-α,α-OH taxane analogs according to the present invention. The sidechain may be replaced, for example, with a compound of Formula 12 according to the generalized Scheme 9, shown in FIG. 12.

Figure 28:
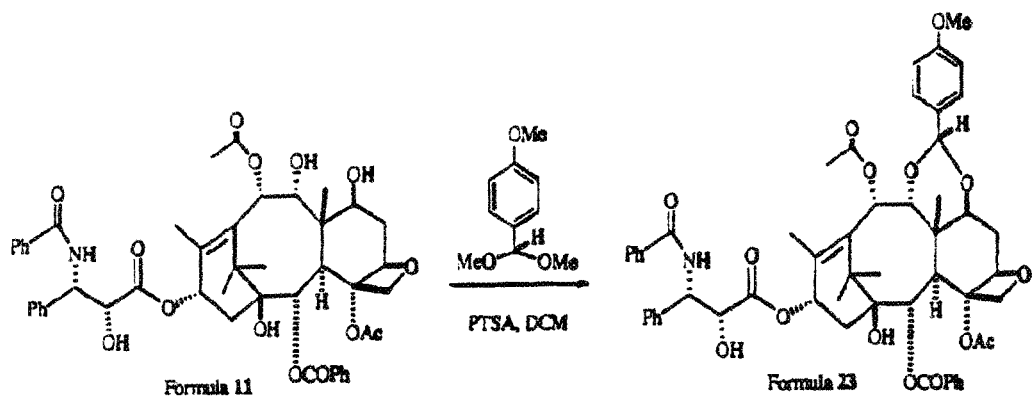
FIG. 28 is a diagram of an exemplary 7,9-acetalization of a compound formed in FIGS. 20 and 21.
Figure 29:
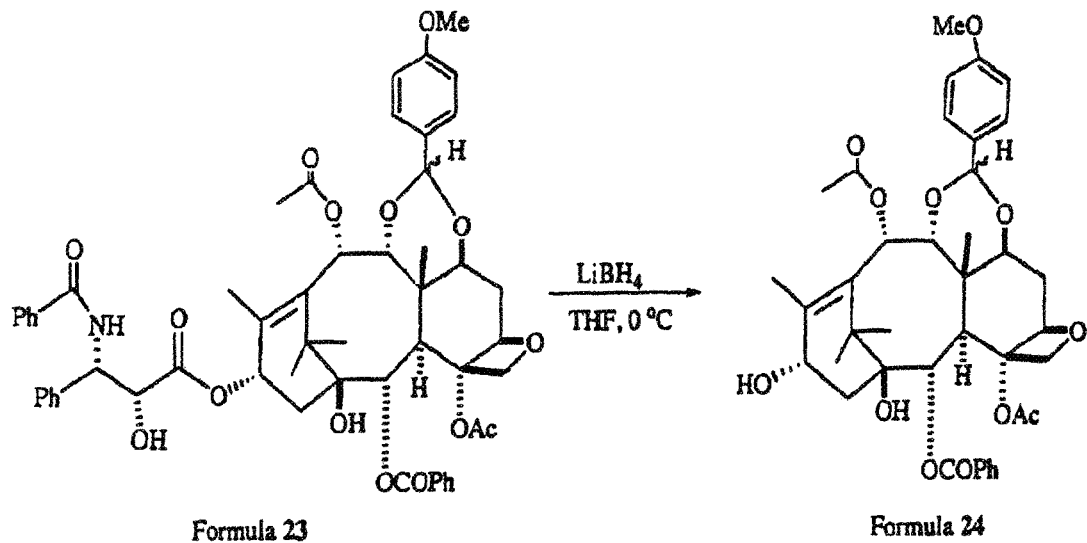
FIG. 29 is a diagram of an exemplary reaction for cleaving the taxane sidechain of the compound formed in FIG. 28.

More particularly, as shown in Scheme 7 and exemplified in FIGS. 28 and 29, a 9,10-α,α-taxane may be protected as a 7,9-acetal linked analog, such as described above, and the sidechain may thereafter be cleaved to provide a 13-hydroxyl taxane. In the compounds shown in Scheme 7, $R_3$ is hydroxyl or $OP_1$; $R_1$, $R_2$, $R_7$ and $P_1$ are as defined above for Scheme 3; and $R_8$ and $R_9$ are as defined above for Scheme 6.

For example, a compound of Formula 11 was first prepared according to procedures described above with respect to FIGS. 18 and 21, as follows. To a 200 mL RBF was charged 5.0 g (4.800 mmol) 2'-O-TBDMS-7-O-TES-9,10-α,α-OH, 9 desoxo 10 deacetyl paclitaxel (Formula 6), 1.75 g (14.400 mmol, 3.0 eq.) DMAP, and 60 mL anhyd. DCM to dissolve the solids. The flask was sealed and placed under nitrogen then the flask was placed in an ice-water bath. Next was slowly charged, 4.5 mL (48.000 mmol, 10.0 eq.) acetic anhydride to the flask. The reaction was stirred at 0° C., going to room temperature overnight. The reaction was quenched after 18 hours by adding 100 mL of saturated sodium bicarbonate solution. Product was extracted with EtOAc and washed with sodium bicarbonate solution and with water. The organic partition was dried down to yield approximately 5.5 g (5.075 mmol) of crude product of Formula 7. This crude product was charged in a 250 mL RBF with 110 mL THF, under nitrogen. Next was charged 14.2 mL of 1.0M TBAF in THF. The reaction was stirred at room temperature for 2.5 hours then was worked up by extracting with EtOAc and washing with water. The organic partition was evaporated to yield approximately 5.9 g of crude solid. The crude material was purified by flash chromatography to yield 1.5 g of purified compound of Formula 11.

As shown for example in FIG. 28, the compound of Formula 11 may be protected as a 7,9-acetal such as with anisaldehyde dimethyl acetal to form a compound of Formula 23 (where $R_1=R_2=Ph$; $R_3=OH$; $R_7=CH_3$; $R_8=H$; $R_9=PhOMe$ in generalized formula Q of Scheme 7). To a 50 mL RBF was charged 1.15 g (1.345 mmol) 9-α-OH-10-epi paclitaxel of Formula 11 and 25 mL anhydrous DCM, under nitrogen. 343 μL (2.017 mmol, 1.5 eq.) anisaldehyde dimethyl acetal was charged to the flask, followed by 51 mg (0.269 mmol, 0.2 eq.) PTSA. The reaction was stirred at room temperature for 45 minutes then was worked up by extracting the product with EtOAc and washing with saturated sodium bicarbonate solution followed by water. The organic partition was evaporated to yield approximately 1.5 g of crude product. The crude product was purified by flash chromatography to yield 0.72 g of pure product of Formula 23.

Next, the sidechain is cleaved to form the compound of Formula 24 (where $R_7=CH_3$; $R_8=H$; $R_9=PhOMe$ in generalized formula R of Scheme 7), as exemplified in FIG. 29. To a 25 mL RBF was charged 720 mg (0.740 mmol) 7,9-anisaldehyde acetal-10-epi paclitaxel of Formula 23 and 15 mL anhyd. THF, under nitrogen. The flask was placed in an ice/water/ammonium chloride, −13° C. bath. Solid lithium borohydride (29.0 mg, 1.331 mmol, 1.8 eq.) was charged to the reaction flask and the reaction stirred at −13° C. for two hours before raising the temperature to 0° C. The reaction was worked up after five hours fifteen minutes by diluting with EtOAc and washing with water and ammonium chloride solution. The organic partition was evaporated to yield 650 mg of crude compound but HPLC indicated that there was only approximately 20% product and mostly unreacted starting material; therefore, the reaction was restarted by repeating the above procedure and running the reaction for an additional six hours. The organic partition was evaporated to yield approximately 660 mg of crude product. The compound was purified on a YMC silica column to yield the compound of Formula 24.

Figure 11:
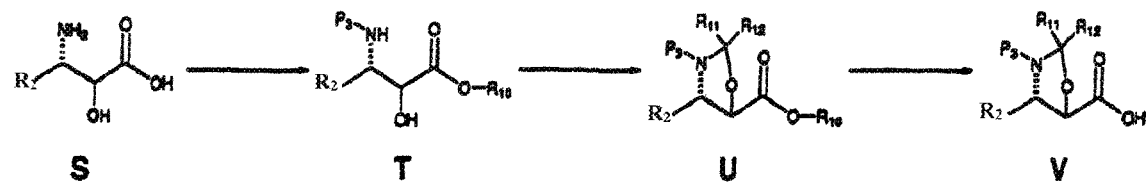
FIG. 11 is a diagram of a generalized Scheme 8 for forming a carboxylic acid for use in attaching an alternative taxane sidechain to 9,10-α,α taxane analogs according to the present invention.
Figure 30:
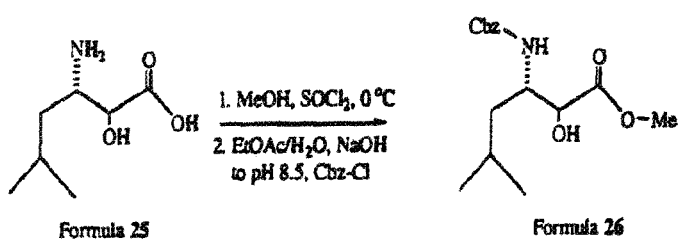
FIG. 30 is a diagram of an exemplary reaction for producing an isobutyl N-protected ester compound for use in forming an alternative taxane sidechain according to the present invention.
Figure 31:
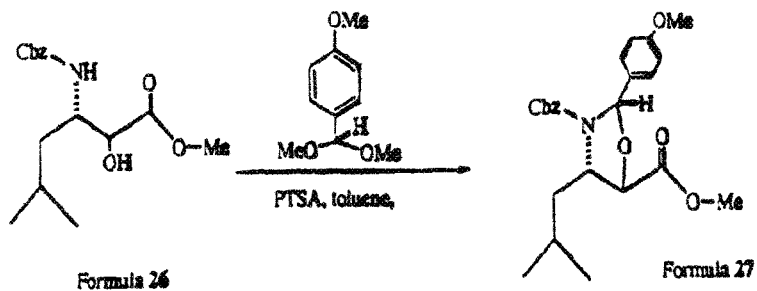
FIG. 31 is a diagram of an exemplary reaction for protecting the compound formed in FIG. 30 as an anisaldehyde acetal.
Figure 32:
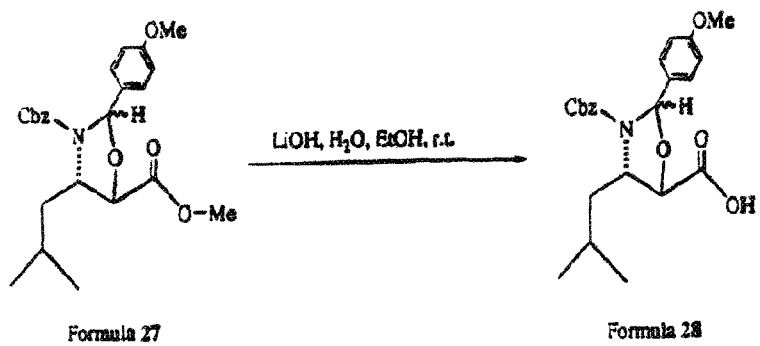
FIG. 32 is a diagram of an exemplary reaction for saponifying the compound formed in FIG. 31 to a carboxylic acid.

The replacement sidechain may next be formed as illustrated in FIG. 11 (Scheme 8) and shown in FIGS. 30 through 32, for example. In the compounds shown in Scheme 8, $R_2$ is as defined above for Schemes 1 and 2; $P_3$ is a hydroxyl protecting group such as a carbobenzyloxy (CBZ) group; $R_{10}$ is an alkyl group such as a methyl or ethyl group; and $R_{12}$ and $R_{12}$ are defined as for $R_8$ and $R_9$, respectively, for Scheme 6 above. It should be appreciated that the $R_2$ group attached at C-3 in Scheme 8 may be different from the $R_2$ group that was on the sidechain that was removed in Scheme 7. Further, while the exemplary diagrams show an isobutyl sidechain, it should be appreciated that other groups may be substituted for the various substituents in the formulas of Scheme 8.

As shown in FIG. 30, a carboxylic acid of Formula 25 (where $R_2=CH_2CH(CH_3)_2$ in generalized formula S of Scheme 8) is converted to an ester of Formula 26 (where $R_2=CH_2CH(CH_3)_2$; $P_3=CBZ$; $R_{10}=$methyl in generalized formula T of Scheme 8). To a 1 L RBF was charged 8.65 g (53.69 mmol) 2-R,S-hydroxy-3-S-amino-5-methyl hexanoic acid of Formula 25, and 130 mL MeOH to suspend the acid. The flask was then placed in an ice-water bath and 17.6 mL (241.62 mmol, 4.5 eq.) thionyl chloride ($SOCl_2$) was slowly charged to the flask. The reaction was stirred at 0° C. for four and a half hours then 160 mL EtOAc and 100 mL water was charged to the flask and the pH of the reaction solution was adjusted to approximately 8 using 3M NaOH. Next, 16.9 mL (118.1 mmol, 2.2 eq.) CBZ—Cl was charged to the flask and the pH was then readjusted to approximately 8. The reaction was stirred an additional three hours before working it up by diluting the reaction with EtOAc, removing the aqueous partition and washing the organic solution with water before evaporating it to yield approximately 22 g of crude oil. The product was purified by normal phase chromatography to yield 8.4 g of product of Formula 26.

As shown in FIG. 31, the compound of Formula 26 may be protected as an N,O-anisaldehyde acetal of Formula 27 (where $R_2=CH_2CH(CH_3)_2$; $P_3=CBZ$; $R_{10}=$methyl; $R_{11}=H$; $R_{12}=PhOMe$ in generalized formula U of Scheme 8). To a 10 mL RBF equipped with a reflux condenser was charged 250 mg (0.809 mmol) 2-R, S-hydroxy-3-S—N-(Cbz)-5-methyl hexanoyl methyl ester and 6 mL toluene to dissolve the solid. Next was charged 15 mg (0.081 mmol, 0.1 eq.) PTSA followed by 165 μL (0.970 mmol, 1.2 eq.) anisaldehyde dimethyl acetal. The reaction was refluxed for two and a half hours then was quenched by washing the reaction solution with 4 mL of saturated sodium bicarbonate solution. The organic partition was evaporated to an oil then was purified by flash chromatography to yield 218 mg of product of Formula 27.

While it is preferred that the N,O-acetal protecting the sidechain is the same as the 7,9-acetal protecting the taxane backbone (i.e. $R_8=R_{11}$ and $R_9=R_{12}$) so that they may both be removed later in a single chemical step, it should be appreciated that different acetal protecting groups may be used, and separate deprotection steps may be necessary.

As shown in FIG. 32, the ester compound of Formula 27 is next saponified to its corresponding carboxylic acid of Formula 28 (where $R_2=CH_2CH(CH_3)_2$; $P_3=CBZ$; $R_{11}=H$; $R_{12}=PhOMe$ in generalized formula V of Scheme 8). To a 5 mL RBF was charged 280 mg (0.656 mmol) of 3-N,2-O-anisaldehyde acetal-3-N-Cbz-5-methyl hexanoyl methyl ester of Formula 27 and 2.8 mL EtOH to dissolve the solid. Next was charged a solution of 51.3 mg LiOH monohydrate in 420 μL water. The reaction was stirred at room temperature for four hours and fifteen minutes then was worked up by quenching with dilute HCl to pH 1 and extracting the product into 20 mL toluene. The organic phase was then washed with water and evaporated to 216 mg of acid product of Formula 28.

As shown in Scheme 9, the replacement sidechain is next coupled to the taxane backbone. In the compounds shown in Scheme 9, $R_2$, $R_{11}$, $R_{12}$ and $P_3$ are as defined above for Scheme 8; $R_7$, $R_8$ and $R_9$ are as defined above for Scheme 7; $R_1$ is as defined above for Schemes 1 and 2; and $R_{13}$ and $R_{14}$ are as defined above for $R_8$ and $R_9$, respectively, of Scheme 6. It should be appreciated that the $R_1$ group in Scheme 9 may be different from the $R_1$ group that was on the sidechain that was removed in Scheme 7.

Figure 33:
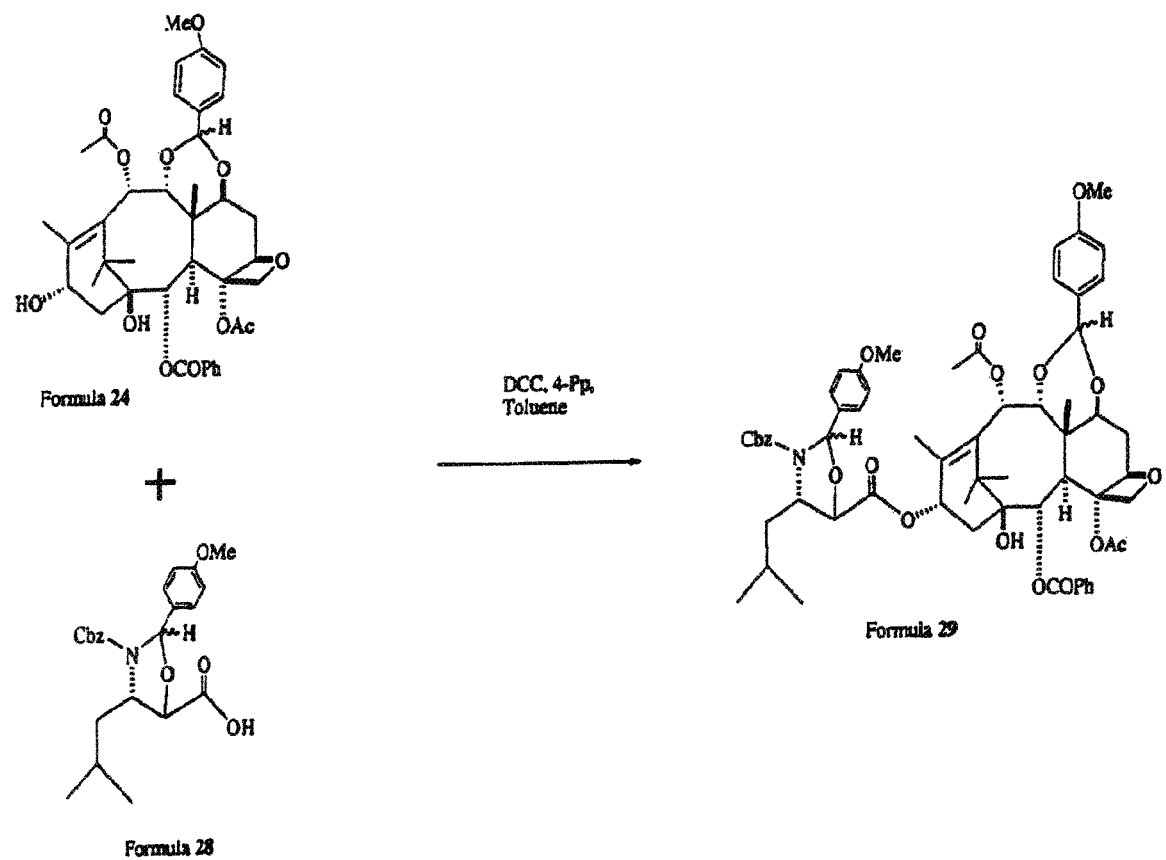
FIG. 33 is a diagram of an exemplary reaction for attaching the sidechain compound formed in FIG. 32 to the 13-hydroxy taxane analog formed in FIG. 29.

FIG. 33, for example, provides the coupling reaction of Formula 24 (from FIG. 29) with Formula 28 (from FIG. 32) to provide the compound of Formula 29 (where $R_2$=CH$_2$CH(CH$_3$)$_2$; $P_3$=CBZ; $R_{11}$=H; $R_{12}$=PhOMe; $R_7$=CH$_3$; $R_8$=H; $R_9$=PhOMe in generalized formula W of Scheme 9). To a 5 mL RBF was charged 180 mg (0.255 mmol) 7,9-anisaldehyde acetal, 9-desoxo 10-epi Baccatin III (Formula 24) and 105 mg (0.510 mmol, 2.0 eq.) DCC. Toluene (2 mL) was then added to dissolve the solids. Next, 158 mg (0.383 mmol, 1.5 eq.) iso-Butyl sidechain acid (Formula 28) was dissolved in 1.0 mL DCM then this solution was charged to the reaction flask followed by 6 mg (0.038 mmol, 0.15 eq.) 4-pp. The reaction was stirred at room temperature for 23 hours then was quenched by adding 11.5 μL acetic acid and 4 μL water and stirring for one hour. MTBE was added to the reaction flask to precipitate DCU and the reaction solution was filtered to remove the precipitate. The filtrate was slurried with activated carbon then passed across a silica plug to remove the 4-Pp salts. The eluent was evaporated to a solid to yield 270.7 mg of crude coupled product of Formula 29.

Figure 34:
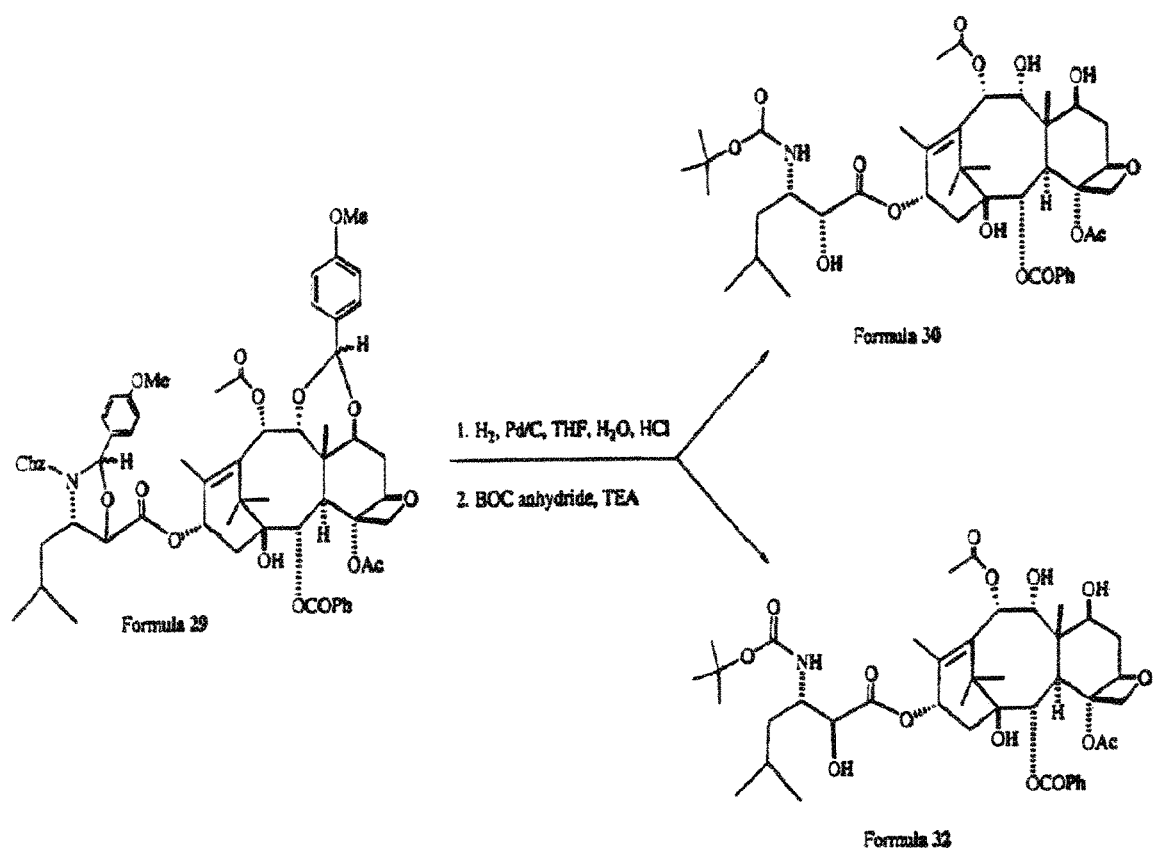
FIG. 34 is a diagram of an exemplary deprotection and acylation of the compound formed in FIG. 33.

As exemplified in FIG. 34, the 7,9-acetal and N,O-acetal protecting groups may then be removed and an N-acyl group added to form the compounds of Formula 30 and 32 (where $R_1$=t-butoxyl; $R_2$=CH$_2$CH(CH$_3$)$_2$; $R_7$=CH$_3$ in generalized formula X of Scheme 9), which may be separated from each other by liquid chromatography or kept together for the next step. While the same anisaldehyde group is used at both the 7,9-acetal and N,O-acetal in the exemplary compound of Formula 29, such that both groups may be removed in a single step, it should be appreciated that other acetal protecting groups are contemplated such that multiple deprotection steps may be required. To a 10 mL RBF was charged, 270 mg (0.245 mmol) of 7,9-anisaldehyde acetal-10-epi-3'-isobutyl-3',2'-N,O-anisaldehyde acetal coupled ester of Formula 29, 220 mg (0.8 g/g coupled ester) Degussa type palladium on carbon, and 4.1 mL THF. In a separate vial, 99 μL conc. HCl was diluted in 1984, water and 1.0 mL THF. This solution was added to the reaction flask and the flask was sealed and placed under hydrogen. The hydrogenation reaction was stirred for 31 hours then was quenched by removing the hydrogen and filtering the catalyst from the reaction solution then adding molecular sieves to the reaction solution to remove water before adding 84.5 μL (0.368 mmol, 1.5 eq.) t-butoxy carbonyl (t-BOC) anhydride then 684 μL TEA. The reaction stirred an additional 21 hours then was worked up by filtering the sieves from the reaction solution, diluting the filtrate with EtOAc and washing with water. The organic partition was evaporated to approximately 370 mg of oil. The oil was purified first by flash chromatography, then preparative TLC (pTLC) then by a semi-prep reverse phase column to yield 3.9 mg of pure product of Formula 30 and 32.

Figure 35:
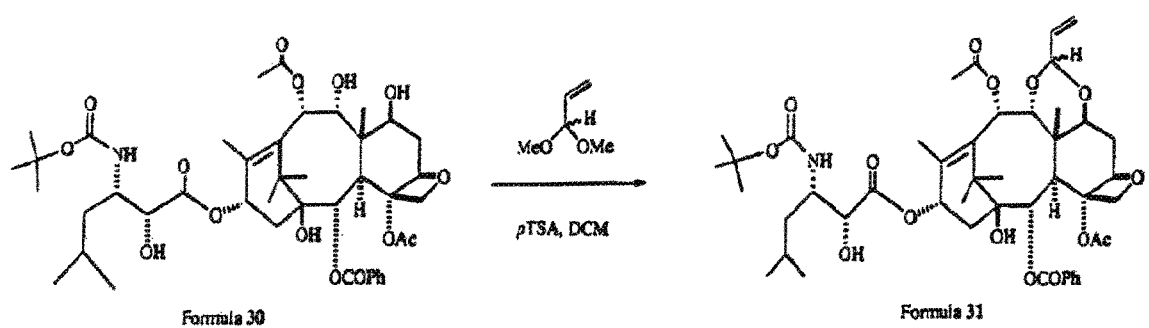
FIG. 35 is a diagram of an exemplary 7,9-acetalization of the compound formed in FIG. 34.
Figure 35:
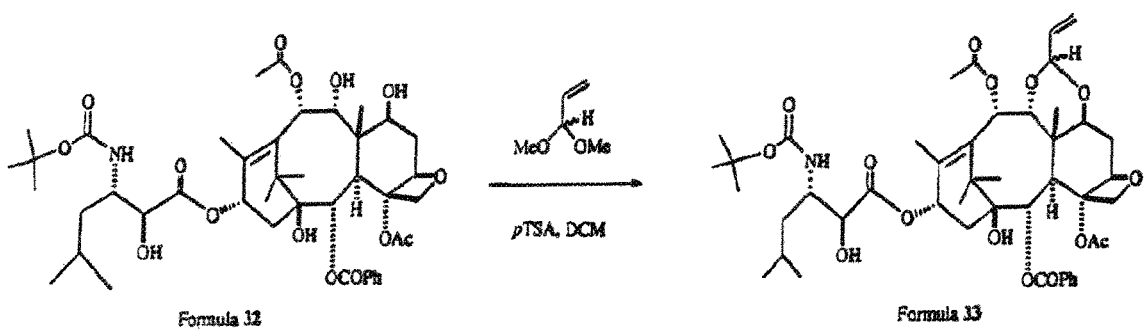

Finally, as shown in FIG. 35, an alternate 7,9-acetal may be formed if desired to provide the compound of Formula 31 or 33 (where $R_1$=t-butyl; $R_2$=CH$_2$CH(CH$_3$)$_2$; $R_7$=CH$_3$; $R_{13}$=H; $R_{14}$=CH=CH$_2$ in generalized formula Y of Scheme 9). While an acrolein acetal is formed in FIG. 35, it should be appreciated that other groups may be substituted for $R_{13}$ and $R_{14}$ of Scheme 9, such as those defined for the $R_8$ and $R_9$ groups exemplified in FIG. 9, or others. In a HPLC vial insert, 3.4 mg (4.13 μmol) of 9-α-hydroxy, 10-α-acetyl-2'-R,S-hydroxy-3'-isobutyl-3'-N-t-butoxy carbonyl taxane of Formula 30 and 32 was charged followed by 70 μL DCM. Next, 12.84, of a 1 to 20 diluted acrolein dimethyl acetal in DCM (0.644, acetal, 5.37 μmol, 1.3 eq.) was charged to the insert followed by 8.4 μL (0.413 μmol, 0.1 eq.) of a 0.05M PTSA solution in DCM. The reaction was lightly agitated then sat at room temperature. The reaction took more additions of the acetal solution to drive it to completion then was worked up after a couple of days by filtering the solution through approximately 80 mg of basic activated alumina. The alumina was washed with DCM then EtOAc and the fractions evaporated to dryness. The crude compound was purified on a normal phase analytical column to yield 605 μg of compound (the product was an isomeric mixture) 7,9-acrolein acetal-10-α-acetyl-2'-R,S-hydroxy-3'-S-isobutyl-3'-N-t-butoxy carbonyl taxane of Formulas 31 and 33, which may be separated by liquid chromatography.

VII. Alternative Method for Synthesizing 7,9-Acetal Linked Analogs 7,9 acetal linked analogs of 9,10-αα OH taxanes can also be formed directly from 10-deacetylbaccatin III (10-DAB), which has the formula:

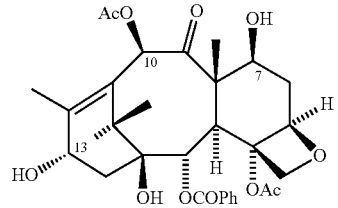

Using 10-DAB has an advantage since it is much more naturally abundant, and thus less expensive than either of the starting compounds A or A' that are shown and discussed above with respect to in FIGS. 1 and 2.

In this alternative process, 10-DAB, Formula 34, is first protected at both the C-7 and C-10 positions to form C7,C10 di-CBZ 10-deacetylbaccatin III, Formula 35, according to the following reaction:

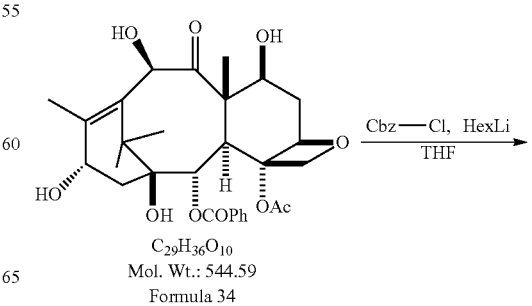

$C_{29}H_{36}O_{10}$
Mol. Wt.: 544.59
Formula 34

33

-continued

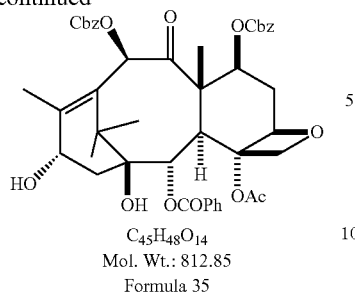

C₄₅H₄₈O₁₄
Mol. Wt.: 812.85
Formula 35

C7,C10 di-CBZ 10-deacetylbaccatin III of Formula 34 (50 g, 91.8 mmol) was dissolved in THF (2 L, 40 ml/g) by warming to 40° C. in a warm-water bath. The solution was cooled to −41° C. in a Neslab chiller and benzylchloroformate (46 mL, 3.2 eq, 293.8 mmol) was added to the stirred chilled solution followed by further cooling to −44° C. To this solution 2.3M hexyl lithium solution (130 mL, 3.3 eq, 303 mmol) was added gradually over 45 min while maintaining the temperature of the reaction mixture at ≤−39° C. Stirring continued in the Neslab for 45 minutes at which time HPLC indicated the reaction had gone to completion. At 2 hr total reaction time, the reaction was quenched by the addition of 1N HCl (400 mL) and IPAc (1 L) and removal from the Neslab chiller. The reaction was allowed to stir while warming to 10° C. The layers were separated and the IPAc layer was washed sequentially with H₂O (500 mL), saturated NaHCO₃ (200 mL) and H₂O (4×500 mL) and then filtered through a silica gel pad. The filtrate was concentrated until solids started to form. IPAc (850 mL) was added and the mixture was heated to 60° C. to dissolve some of the solids. To the warm solution, heptanes (800 mL) were added and the solution was cooled in the refrigerator and filtered. The solids collected by the filtration were washed with heptanes and dried under vacuum at 45° C. to give 35.

Next, Formula 35 was coupled with a sidechain of Formula 36 to form Formula 37 according to the following reaction:

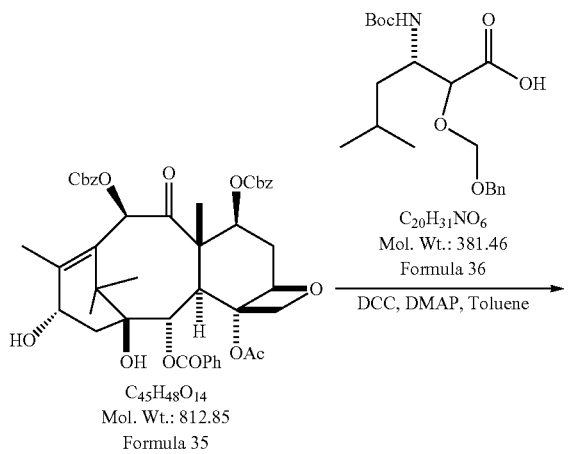

34

-continued

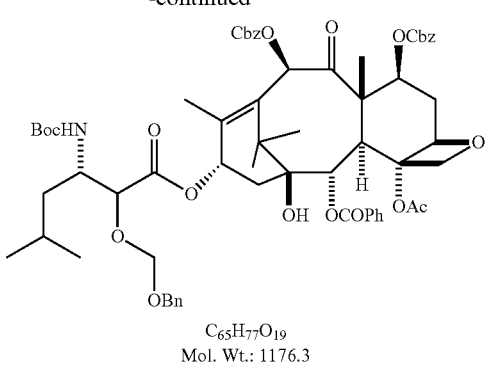

C₆₅H₇₇O₁₉
Mol. Wt.: 1176.3
Formula 37

Here, the sidechain of Formula 36, (38 g, 99.6 mmol) was dissolved in toluene to a known concentration (0.09524 g/mL). This solution was added to Formula 35 (54.0 g, 66.4 mmol). The solution was heated in a warm-water bath and DMAP (8.13 g, 66.4 mmol) and DCC (25.28 g, 119.6 mmol) in toluene (540 mL) were added to the warm reaction mixture. While maintaining the temperature at about 51° C., the reaction was continually stirred and sampled periodically for HPLC. After 3 hours, additional DCC (13.0 g) in toluene (140 mL) was added.

The following morning (25.25 hr), MTBE (450 mL) was added and the reaction mixture was filtered through a pad of silica gel, washed with MTBE followed by EtOAc, and concentrated to give 61.8 g oil. The silica was washed again with EtOAc and the second pool was concentrated to 50 mL and allowed to sit. The following day the second pool had started to crystallize. It was filtered and the filtrate was washed with 1:1 heptane/IPAc and dried under vacuum at 40° C. to give a solid of Formula 37.

Next, Formula 37 was deprotected at both the C7 and C10 position to give Formula 38 according to the following reaction:

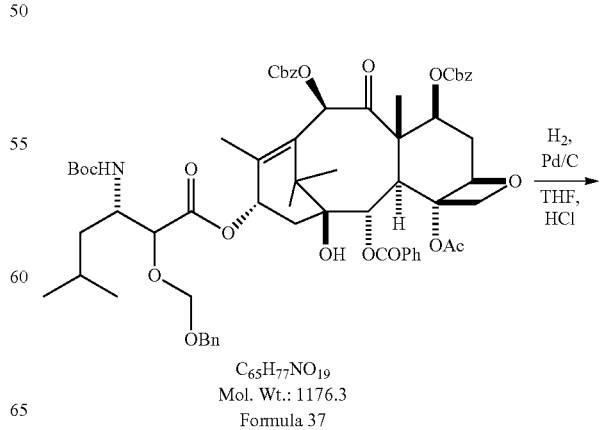

C₆₅H₇₇NO₁₉
Mol. Wt.: 1176.3
Formula 37

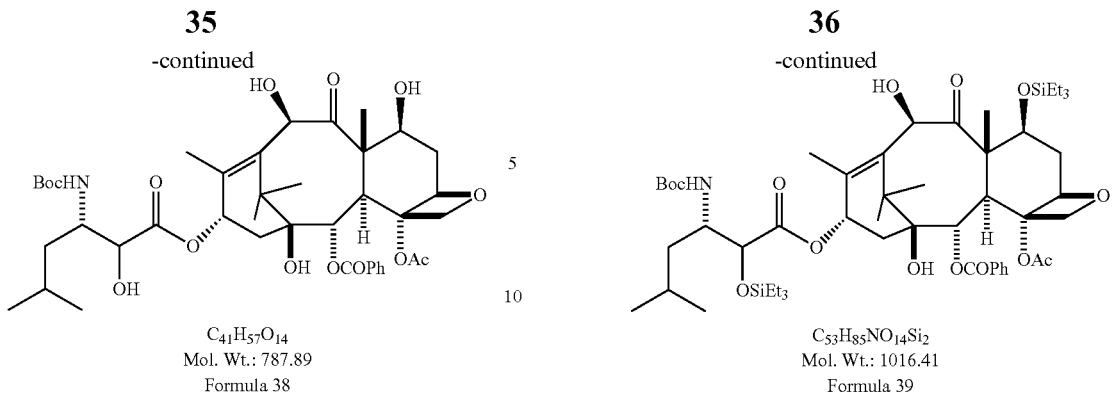

C₄₁H₅₇O₁₄
Mol. Wt.: 787.89
Formula 38

C₅₃H₈₅NO₁₄Si₂
Mol. Wt.: 1016.41
Formula 39

A solution of THF (300 mL) and HCl (22 mL) was added to a solution of Formula 37 (61.8, 52.5 mmol) in THF (15 mL/g, 920 mL). The resulting solution was flushed with nitrogen. A catalyst (10% Pd/C with 50% water, 99.1 g) was added and the flask was flushed with nitrogen three times and then with hydrogen three times. The reaction mixture was stirred vigorously under a hydrogen balloon for 21 hours. At this time the reaction was sampled and HPLC indicated that 38% by area of starting material still remained. Water (10 mL) was added and stirring continued. Twenty hours later, HPLC indicated the same amount of starting material still remaining. The reaction mixture was filtered through celite and washed with THF. It was then concentrated to remove excess THF; fresh catalyst (101 g) was added and the reaction mixture was placed back under hydrogen as before. After another 24 hours, an intermediate compound was still present and still more catalyst (20 g) was added. After another hour, HPLC indicated that the reaction was complete. The reaction mixture was filtered through celite and washed through with IPAc. The combined filtrate was washed with NH₄Cl solution (500 mL), water (500 mL), 5% NaHCO₃ (500 mL), H₂O (300 mL), and brine (300 mL). The organic layer was dried, filtered, and concentrated to give a foam of Formula 38.

Formula 38 was then converted to Formula 39 according to the following reaction:

Formula 38 (41.37 g, 52.5 mmol) was dissolved in DCM (500 mL) at room temperature. The solution was cloudy, possibly caused by the presence of DCU in the product from the previous reaction. In the case that the impurity was water, Na₂SO₄ was added to the solution, and the solution was filtered through filter paper into to a 2 L flask. The solids were collected and washed with DCM (250 mL) into the flask and the flask was covered with a septum and N₂ balloon. Tea (35 mL) followed by DMAP (1.284 g) and TES-Cl (~30 mL, 3.5 eq) were added to the solution and stirred. Additional TES-Cl (15 mL) and TEA (20 mL) were added, and after 6 hours HPLC indicated the reaction had gone to completion.

The reaction was then quenched by the addition of EtOH (25 mL). The layers were separated and the organic layer was washed with saturated NH₄Cl (~500 mL) and dried over Na₂SO₄ and concentrated. A flash column was packed with silica gel and wet with 8:2 heptane/IPAc (1.5 L). The solids were dissolved in 8:2 heptane/IPAc (250 mL) and filtered to remove solids that would not dissolve. This solution was concentrated to ~100 mL and applied to the column. The column was eluted with 8:2 heptane/IPAc and fractions collected. Fractions with product were pooled and concentrated to give foam of Formula 39.

Formula 39 was then oxidized to form Formula 40 according to the following reaction:

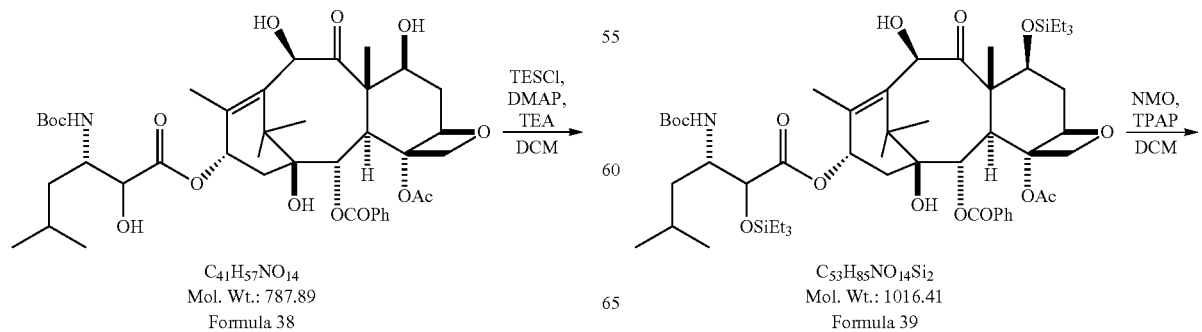

C₄₁H₅₇NO₁₄
Mol. Wt.: 787.89
Formula 38

C₅₃H₈₅NO₁₄Si₂
Mol. Wt.: 1016.41
Formula 39

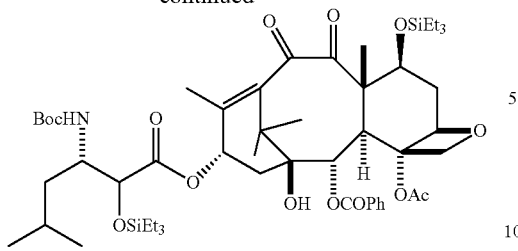

C$_{53}$H$_{83}$NO$_{14}$Si$_2$
Mol. Wt.: 1014.4
Formula 40

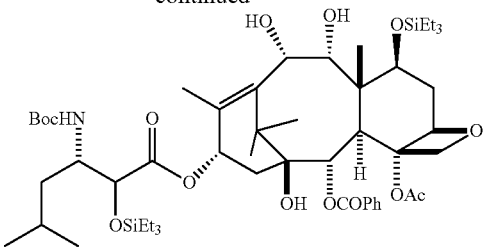

C$_{53}$H$_{87}$NO$_{14}$Si$_2$
Mol. Wt.: 1018.43
Formula 41

Here, solid Na$_2$SO$_4$ was added to a solution of Formula 39 (24.45 g, 24.0 mmol) and 4-methyl morpholine N-oxide (10.1 g, 84 mmol) in DCM (340 mL) to assure that the reaction was dry. The mixture was stirred for 1 hour and then filtered through 24 cm fluted filter paper into a 2 L 3-N round bottom flask. The Na$_2$SO$_4$ solids were washed with DCM (100 mL) into the flask. Molecular sieves (6.1 g, 15 wt %/g) were added to the solution and stirring was begun. TPAP (1.38 g) was added and the reaction was allowed to stir under a N$_2$ blanket. Samples were taken periodically for HPLC. Additional TPAP (0.62 g) was added after 2 hours and again (0.8 g) after 15 hours. The reaction mixture was applied to a pad of silica gel (86 g), wet with 8:2 heptane/IPAc and eluted with IPAc. The fractions were collected, pooled and concentrated to an oil. 4-Methyl morpholine N-oxide (5.0 g) and DCM (100 mL) were added and stirred. Na$_2$SO$_4$ (13 g) was added to the mixture and it was filtered through filter paper. The Na$_2$SO$_4$ solids were washed with DCM (45 mL) and molecular sieves (5 g) and TPAP (1.03 g) were added. After 45 minutes, more TPAP (1.05 g) was added. A pad of silica gel was prepared and wet with 80:20 Heptane/IPAc. The reaction mixture was applied to the pad and eluted with IPAc. Fractions were collected and those fractions containing product were pooled and concentrated to give an oil product of Formula 40.

Next, Formula 40 was reduced according to the following reaction to form Formula 41.

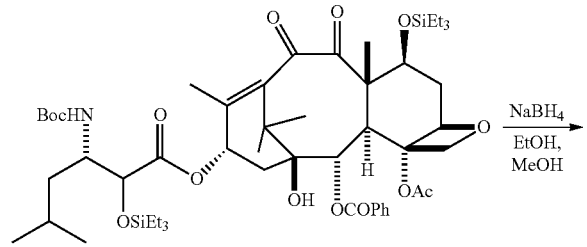

C$_{53}$H$_{83}$NO$_{14}$Si$_2$
Mol. Wt.: 1014.4
Formula 40

NaBH$_4$ (365 mg, 6 eq) was added to a stirred solution of Formula 40 (1.6 g) in EtOH (19 mL) and MeOH (6.5 mL) cooled in an ice-water bath. After 1 hour, the reaction mixture was removed from the ice-water bath and at 2 hours, the reaction was sampled for HPLC, which indicated the reaction had gone to completion. The reaction mixture was cooled in an ice-water bath and a solution of NH$_4$OAc in MeOH (15 mL) was added followed by the addition of IPAc (50 mL) and H$_2$O (20 mL). It was mixed and separated. The organic layer was washed with water (20 mL) and brine (10 mL), a second time with water (15 mL) and brine (10 mL), and then twice with water (2×15 mL). It was dried over Na$_2$SO$_4$ and placed in the freezer overnight. The following morning a sample was taken for HPLC and the reaction was dried and the organic layer was concentrated on the rotovap. It was placed in the vacuum oven to give a foam product of Formula 41.

Formula 41 was next acylated to form Formula 42 according to the following reaction:

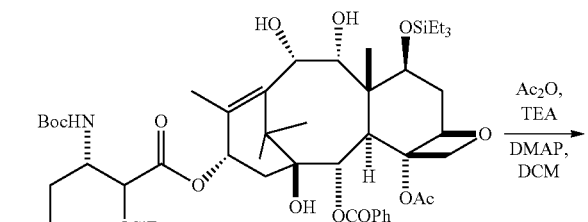

C$_{53}$H$_{87}$NO$_{14}$Si$_2$
Mol. Wt.: 1018.43
Formula 41

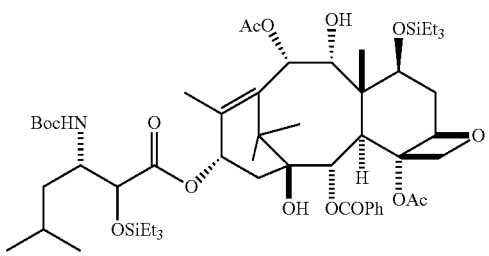

C$_{55}$H$_{89}$NO$_{15}$Si$_2$
Mol. Wt.: 1060.46
Formula 42

TEA (5.8 mL, 41.5 mmol), Ac$_2$O (2.62 mL, 27.7 mmol) and DMAP (724 mg, 5.5 mmol) were added to a solution of Formula 41 (14.1 g. 13.84 mmol)) in DCM (50 mL). The reaction was stirred and sampled for HPLC periodically.

After 18.5 hours, additional TEA (1.5 mL) and Ac₂O (1 mL) were added. At 19 hours, HPLC indicated the reaction had gone to completion. The reaction mixture was diluted with IPAc (300 mL) and poured into 5% HaHCO₃ (100 ml). It was then stirred, separated, and the organic layer was washed with water (100 mL), saturated NH₄Cl (2×100 mL), water (3×50 mL) and brine (50 mL) and then filtered through Na₂SO₄. The mixture was concentrated to give a foam product of Formula 42.

Next, Formula 42 was converted to a compound of Formula 43 according to the following reaction:

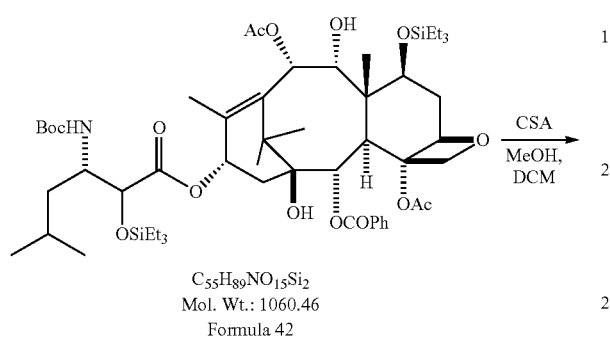

C₅₅H₈₉NO₁₅Si₂
Mol. Wt.: 1060.46
Formula 42

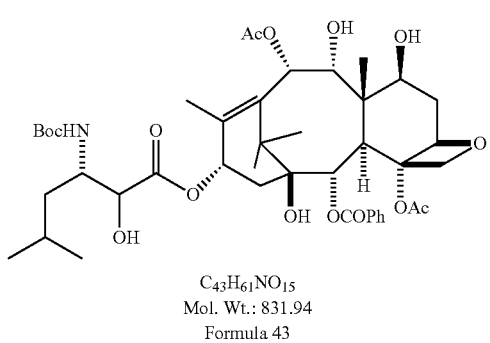

C₄₃H₆₁NO₁₅
Mol. Wt.: 831.94
Formula 43

A quantity of Formula 42 (3.0 g, 2.829 mmol) was weighed into a 100 mL flask. Next, DCM (24 mL) followed by MeOH (6 mL) were added to the flask at room temperature. Stirring of the mixture began under N₂ and CSA (0.0394 g, 0.17 mmol) was added. After 4 hours LCMS indicated the product had formed. 5% NaHCO₃ (15 mL) was added to the reaction mixture; it was shaken vigorously and then added to a separatory funnel. The reaction flask was rinsed into the separatory funnel with 5% NaHCO₃ (25 mL) and, thereafter, the reaction mixture was shaken and the layers were separated. The organic layer was washed with brine, dried over Na₂SO₄, and concentrated. MTBE (3×25 mL) was added and the reaction mixture was concentrated to dryness after each addition to finally give 3.7068 g foam. The foam was dissolved in MTBE (10 mL) and stirred. Heptane (50 mL) was slowly added to the reaction solution and solids began to form immediately. The solids were vacuum filtered and rinsed with heptane (720 mL). The solids were collected and dried in a vacuum oven at 40° C. to give Formula 43.

Formula 43 was then converted to Formula 44 in the following reaction:

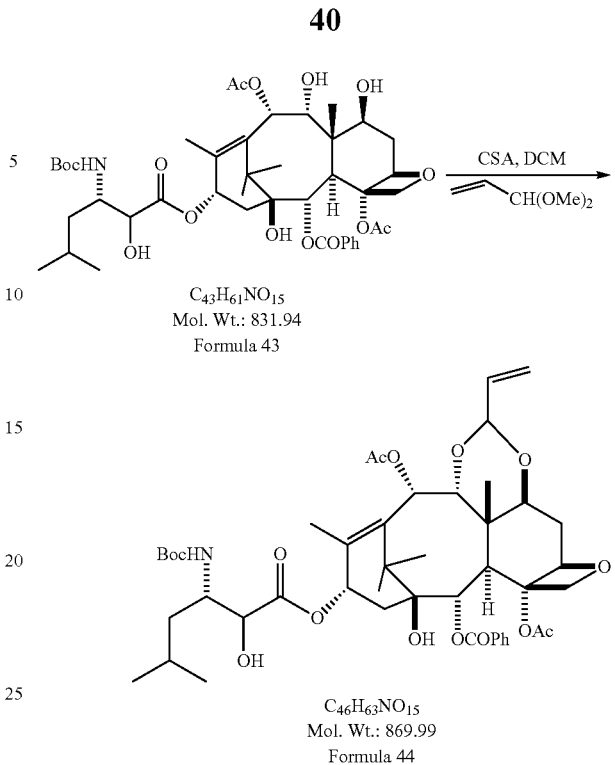

A solution of Formula 43 (2.1 g, 2.52 mmol) in DCM (10.5 mL) was stirred at room temperature. Next, 3,3-dimethoxy-1-propene (2.03 g, 17.7 mmol) followed by CSA (0.035 g, 0.15 mmol) were added to the solution. After the solution was stirred for 3.5 hours, LCMS indicated the reaction had gone to completion. The reaction was diluted with DCM (25 mL) and added to a separatory funnel with 55 mL 5% NaHCO₃ solution. The layers were separated and the aqueous layer was washed with DCM (25 mL). The two organic layers were combined, washed with brine, dried over Na₂SO₄ and concentrated. A flash chromatography column was packed with silica gel and wet with 50:50 MTBE/heptane (1000 mL). The reaction mixture was dissolved in MTBE (10 mL), loaded on the column and eluted with 50:50 MTBE/heptane. The fractions were collected, pooled, concentrated and dried in a vacuum oven at 50° C. to give product of Formula 44.

IX. Alternate Sidechain Coupling Reaction

As illustrated above in the second reaction step of the alternative process of forming 7,9 acetal linked analogs of 9,10-αα OH taxanes, the C7,C10 di-CBZ 10-deacetylbaccatin III of Formula 35 was coupled with a sidechain of Formula 36 to form Formula 37. The present invention further contemplates the coupling of an alternative sidechain to Formula 35. The alternative sidechain of Formula 45 that is contemplated has the following structure:

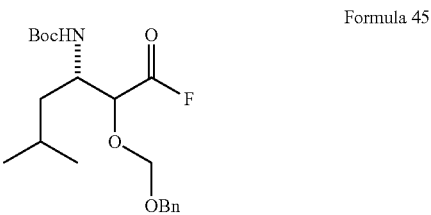 [SMILES: CC(C)C[C@H](NC(=O)OC(C)(C)C)C(OCOCc1ccccc1)C(=O)F]

Formula 45

Formula 45 may be formed from the structure of Formula 36 (above) according to the following reaction:

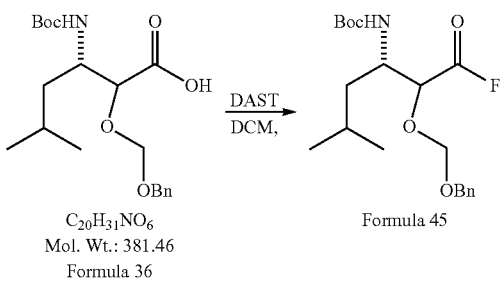

C$_{20}$H$_{31}$NO$_6$
Mol. Wt.: 381.46
Formula 36

Formula 45

Here, the BOM-acid, Formula 36, (3.8 g, ~10.0 mmol) was dissolved in DCM (30 mL), stirred and cooled in an ice-water bath at 0° C. under N$_2$. DCM (2 mL) and diethyl sulfur trifluoride (1.575 g, 20.0 mmol) were both added to this solution and the reaction was stirred for 4 hours. The temperature increased to about 10° C. LCMS indicated the reaction had gone to completion. H$_2$O (50 mL) and DCM (50 mL) were added and the reaction mixture was transferred to a separatory funnel. The layers were separated and the organic layer was washed with H$_2$O (50 mL) and brine (50 mL), dried over Na$_2$SO$_4$ and concentrated yielding product of Formula 45.

Next, Formula 35 was coupled with a sidechain of Formula 45 resulting in product of Formula 46 according to the following reaction:

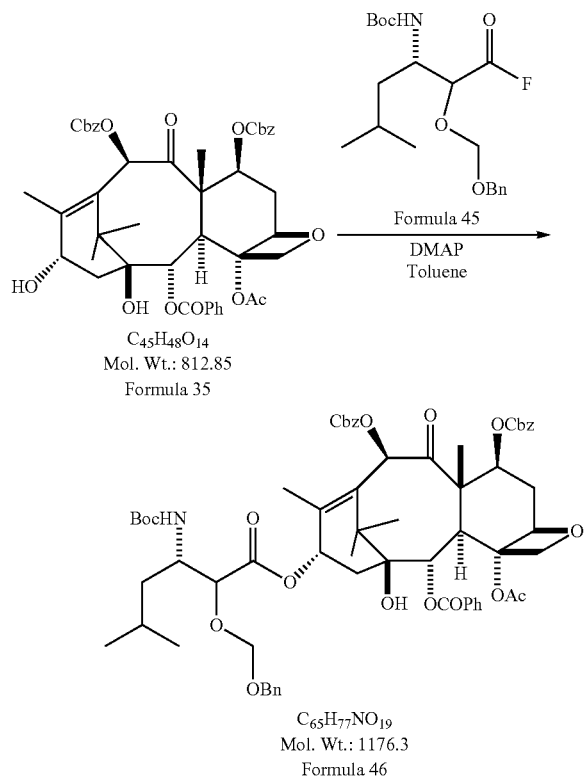

C$_{45}$H$_{48}$O$_{14}$
Mol. Wt.: 812.85
Formula 35

C$_{65}$H$_{77}$NO$_{19}$
Mol. Wt.: 1176.3
Formula 46

Here, Formula 35 (0.2 g, 0.246 mmol) and DMAP (0.5 g, 4.1 mmol) were weighed into a pear shaped flame-dried flask purged with N$_2$. An oven-dried reflux condenser, purged with N$_2$, was placed on top of the flask and it was put in an oil bath heated to 75° C. The BOM acyl fluoride, Formula 45 (0.5 g, 1.31 mmol), in toluene (1 mL) was added to the flask and the temperature increased to 85° C. Stirring continued under N$_2$ for 5.5 hour to give product of Formula 46.

Accordingly, the present invention has been described with some degree of particularity directed to the exemplary embodiments of the present invention. It should be appreciated, though, that the present invention is defined by the following claims construed in light of the prior art so that modifications or changes may be made to the exemplary embodiments of the present invention without departing from the inventive concepts contained herein.

We claim:

1. A composition for treating cancer comprising a taxane derivative, said derivative having an acetal bridge between the hydroxyl groups at the 7- and 9-ring positions and having α stereochemistry at the 9- and 10-ring positions, wherein the acetal bridge has the structure —OC(R$_8$)(R$_9$)O—, wherein R$_8$ is H and R$_9$ is

2. The composition for the treatment according to claim 1 characterized in that the cancer is selected from the group consisting of Ovarian Carcinoma, Breast Cancer, Neuroblastoma and Squamous Cell Carcinoma.

3. The composition for the treatment according to claim 1 characterized in that the cancer is Ovarian Carcinoma.

4. The composition for the treatment according to claim 1 characterized in that the cancer is Breast Cancer.

5. The composition for the treatment according to claim 1 characterized in that the cancer is Neuroblastoma.

6. The composition for the treatment according to claim 1 characterized in that the cancer is Squamous Cell Carcinoma.

7. A composition comprising a taxane derivative, said derivative having an acetal bridge between the hydroxyl groups at the 7- and 9-ring positions and having α stereochemistry at the 9- and 10-ring positions, wherein the acetal bridge has the structure —OC(R$_8$)(R$_9$)O—, wherein R$_8$ is H and R$_9$ is

8. The composition according to claim 7, wherein said acetal bridge is part of a fused four member ring system.

9. The composition according to claim 8, wherein there is β, α stereochemistry at the 7- and 9-ring positions of the fused four member ring system.

10. The composition according to claim 8, wherein the β-ring position is a group having the structure:

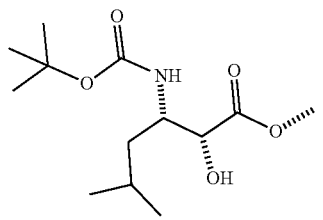
and having α stereochemistry at the β-ring position of the fused four member ring system, wherein there are AcO groups having α, α stereochemistry at the 4- and 10-ring positions of the fused four member ring system.
* * * * *